(12) United States Patent
Dahl et al.

(10) Patent No.: US 11,078,529 B2
(45) Date of Patent: Aug. 3, 2021

(54) METHODS AND KITS FOR DETECTION OF METHYLATION STATUS

(71) Applicant: OSLO UNIVERSITETSSYKEHUS HF, Oslo (NO)

(72) Inventors: John Arne Dahl, Oslo (NO); Adam Brian Robertson, Oslo (NO); Arne Klungland, Oslo (NO); Linda Ellevog, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 0 days.

(21) Appl. No.: 16/009,835

(22) Filed: Jun. 15, 2018

(65) Prior Publication Data
US 2018/0291442 A1    Oct. 11, 2018

Related U.S. Application Data

(63) Continuation of application No. 14/363,442, filed as application No. PCT/US2012/069525 on Dec. 13, 2012, now Pat. No. 10,023,909.

(60) Provisional application No. 61/570,066, filed on Dec. 13, 2011.

(51) Int. Cl.
C12Q 1/6869    (2018.01)
C12Q 1/6844    (2018.01)

(52) U.S. Cl.
CPC ......... *C12Q 1/6869* (2013.01); *C12Q 1/6846* (2013.01)

(58) Field of Classification Search
CPC ............................ C12Q 1/6869; C12Q 1/6846
See application file for complete search history.

(56) References Cited

U.S. PATENT DOCUMENTS

| | | | |
|---|---|---|---|
| 8,653,007 B2 | 2/2014 | Zheng et al. |
| 8,679,745 B2 | 3/2014 | Ballhause et al. |
| 8,741,567 B2 | 6/2014 | He et al. |
| 8,822,146 B2 | 9/2014 | Klimasauskas et al. |
| 8,889,352 B2 | 11/2014 | Klimasauskas et al. |
| 8,951,736 B2 | 2/2015 | Schmidt |
| 8,962,246 B2 | 2/2015 | Ballhause et al. |
| 8,969,061 B2 | 3/2015 | Zhu et al. |
| 9,029,087 B2 | 5/2015 | Zheng et al. |
| 9,034,597 B2 | 5/2015 | Bitinaite et al. |

(Continued)

FOREIGN PATENT DOCUMENTS

| | | |
|---|---|---|
| EP | 1568786 A2 | 8/2005 |
| EP | 2376632 A1 | 10/2011 |

(Continued)

OTHER PUBLICATIONS

GenBank: AAI44094.1. Jan. 8, 2009. (Year: 2009).*

(Continued)

*Primary Examiner* — Joseph G. Dauner
(74) *Attorney, Agent, or Firm* — Casimir Jones S.C.; J. Mitchell Jones

(57) ABSTRACT

The present invention relates to methods and kits for the detection of 5-hydroxymethylcytosine (5hmC) and/or 5-methylcytosine (5meC). In some embodiments, the present invention relates to methods and kits for detection of 5hmC and/or 5meC in nucleic acid (e.g., DNA, RNA). In some embodiments, the present invention relates to detection of 5hmC in genomic DNA, e.g., mammalian genomic DNA.

15 Claims, 13 Drawing Sheets

Specification includes a Sequence Listing.

(56) References Cited

U.S. PATENT DOCUMENTS

| | | |
|---|---|---|
| 9,040,239 B2 | 5/2015 | Zheng et al. |
| 9,121,061 B2 | 9/2015 | Vaisvila et al. |
| 9,145,580 B2 | 9/2015 | Feehery et al. |
| 9,150,918 B2 | 10/2015 | Turner et al. |
| 9,175,338 B2 | 11/2015 | Flusberg et al. |
| 9,175,341 B2 | 11/2015 | Flusberg et al. |
| 9,175,348 B2 | 11/2015 | Korlach et al. |
| 9,200,260 B2 | 12/2015 | Correa, Jr. et al. |
| 9,200,316 B2 | 12/2015 | Zheng et al. |
| 9,238,836 B2 | 1/2016 | Korlach et al. |
| 9,243,233 B2 | 1/2016 | Rim et al. |
| 9,267,117 B2 | 2/2016 | Guan et al. |
| 9,347,093 B2 | 5/2016 | Klimasauskas et al. |
| 9,464,277 B2 | 10/2016 | Zheng et al. |
| 9,505,797 B2 | 11/2016 | Klimasauskas et al. |
| 9,546,400 B2 | 1/2017 | Turner et al. |
| 9,567,633 B2 | 2/2017 | Gao et al. |
| 9,611,510 B2 | 4/2017 | He et al. |
| 9,650,675 B2 | 5/2017 | Rimseliene et al. |
| 9,677,128 B2 | 6/2017 | Robertson et al. |
| 9,879,315 B2 | 1/2018 | Summerer et al. |
| 9,915,655 B2 | 3/2018 | Bensimon et al. |
| 9,988,673 B2 | 6/2018 | Klimasauskas et al. |
| 10,081,827 B2 | 9/2018 | Guan et al. |
| 10,155,939 B1 | 12/2018 | Vaisvila et al. |
| 2004/0048279 A1 | 3/2004 | Olek et al. |
| 2004/0054162 A1 | 3/2004 | Hanna |
| 2005/0153296 A1 | 7/2005 | Berlin et al. |
| 2006/0257905 A1 | 11/2006 | Freije et al. |
| 2007/0026393 A1 | 2/2007 | Berlin et al. |
| 2007/0238117 A1 | 10/2007 | Rajeevan et al. |
| 2007/0269824 A1 | 11/2007 | Albrecht et al. |
| 2010/0167942 A1 | 7/2010 | Zheng et al. |
| 2010/0197510 A1 | 8/2010 | Spain et al. |
| 2011/0059432 A1 | 3/2011 | Ballhause et al. |
| 2011/0301045 A1 | 12/2011 | He et al. |
| 2012/0064521 A1 | 3/2012 | Yen et al. |
| 2013/0230856 A1 | 9/2013 | Schneider et al. |
| 2014/0178873 A1 | 6/2014 | Brachmann et al. |
| 2014/0179564 A1 | 6/2014 | Korlach et al. |
| 2014/0272970 A1 | 9/2014 | Zegzouti et al. |
| 2015/0004596 A1 | 1/2015 | Zhu et al. |
| 2015/0011403 A1 | 1/2015 | Lo et al. |
| 2015/0056616 A1 | 2/2015 | He et al. |
| 2015/0240310 A1 | 8/2015 | Bitinaite et al. |
| 2015/0285807 A1 | 10/2015 | Shi et al. |
| 2015/0307542 A1 | 10/2015 | Roy et al. |
| 2016/0046981 A1 | 2/2016 | Correa, Jr. et al. |
| 2016/0115525 A1 | 4/2016 | Ebenstein et al. |
| 2016/0194696 A1 | 7/2016 | Guan et al. |
| 2016/0304552 A1 | 10/2016 | Roy et al. |
| 2017/0051354 A1 | 2/2017 | Davis et al. |
| 2017/0067093 A1 | 3/2017 | Klimasauskas et al. |
| 2017/0175129 A1 | 6/2017 | Roy et al. |
| 2017/0198344 A1 | 7/2017 | Vaisvila et al. |
| 2017/0253924 A1 | 9/2017 | Lu et al. |
| 2017/0283863 A1 | 10/2017 | Robertson et al. |
| 2017/0298422 A1 | 10/2017 | Song et al. |
| 2018/0105884 A1 | 4/2018 | Lo et al. |
| 2018/0112206 A1 | 4/2018 | Forsyth |
| 2018/0171397 A1 | 6/2018 | Vaisvila et al. |
| 2018/0201993 A1 | 7/2018 | Turner et al. |
| 2018/0245128 A1 | 8/2018 | He et al. |
| 2018/0251815 A1 | 9/2018 | Okamoto et al. |
| 2018/0258149 A1 | 9/2018 | Motz et al. |
| 2018/0258474 A1 | 9/2018 | Jain et al. |
| 2018/0312914 A1 | 11/2018 | Vaisvila et al. |
| 2018/0327855 A1 | 11/2018 | Ebenstein et al. |
| 2019/0017109 A1 | 1/2019 | Song et al. |

FOREIGN PATENT DOCUMENTS

| | | |
|---|---|---|
| EP | 2414527 A1 | 2/2012 |
| EP | 2414528 A1 | 2/2012 |
| EP | 2470675 A1 | 7/2012 |
| EP | 2630257 A1 | 8/2013 |
| EP | 2694686 A2 | 2/2014 |
| EP | 2776575 A1 | 9/2014 |
| EP | 2825645 A2 | 1/2015 |
| EP | 2948774 A1 | 12/2015 |
| EP | 3013979 A1 | 5/2016 |
| EP | 3053585 A1 | 8/2016 |
| EP | 3124605 A1 | 2/2017 |
| EP | 3214183 A1 | 9/2017 |
| WO | WO-2009092035 A2 | 7/2009 |
| WO | WO-2018129120 A1 | 7/2018 |
| WO | WO-2018165459 A1 | 9/2018 |

OTHER PUBLICATIONS

GenBank: P15840.3. Published Oct. 5, 2010. (Year: 2010).*
Huang et al. PLoS ONE. 2010. 5(1):e8888, 9 pages. (Year: 2010).*
Flusberg, B.A. et al., Direct detection of DNA methylation during single-molecule, real-time sequencing. Nat Methods 7, 461-465 (2010).
Georgopoulos, C.P. et al., Studies with glucosyl transferase mutants of the T-even bacteriophages. Virology 44, 271-285(1971).
Munzel, et al., 5-Hydroxymethylcytosine, the sixth base of the genome. Agnew Chem Intl Ed. Engl, vol. 50, Issue 29, 6460-6468 (2011).
Nestor, et al., Enzymatic approaches and bisulfite sequencing cannot distinguish between 5-methylcytosine and 5-hydroxymethylcytosine in DNA. Biotechniques 48, 317-319 (2010).
Robertson, A.B. et al. A novel method for the efficient and selective identification of 5-hydroxymethylcytosine in genomic DNA. Nucleic acids research 39, e55 (2011).
Sabatini, R. et al., Recognition of base J in duplex DNA by J-binding protein. J Biol Chem 277, 958-966 (2002).
Song, C.X., et al. Detection of 5-hydroxymethylcytosine in a combined glycosylation restriction analysis (CGRA) using restriction enzyme Taq(alpha)I. Bioorg Med Chem Lett (2011).
Song, C.X. et al., Selective chemical labeling reveals the genome-wide distribution of 5-hydroxymethylcytosine. Nature biotechnology 29, 68-72 (2011).
International Search Report and Written Opinion, International Patent Application No. PCT/US2012/069525, dated Dec. 13, 2012 (17 Pages).
Valinluck et al. "Endogenous Cytosine Damage Products Alter the Site Selectivity . . . " Cancer Res. 2007. 67:946-350.
Song, Chun-Xiao et al., "The hunt for 5-hydroxymethylcytosine: the sixth base", Epigenomics, vo. 3, No. 5, 521-523, Oct. 1, 2011.
European Search Report dated Oct. 10, 2018 for EP Application No. 18174572.
Takahashi, Saori et al., "A novel method to analyze 5-hydroxymethylcytosine in CpG sequences using maintenance DNA methyltransferase, DNMT1", FEBS Open Bio, vol. 5, No. 1, 741-747, Jan. 1, 2015.

* cited by examiner

5hmC Dilution Assay (A) -T-C-G-A-T-5meC-G-A-T-5hmC-G-T-
-A-G-C-T-A-G-5meC-T-A-G-5hmC-A-
(SEQ ID NO:10)

① 1 x cycle of PCR

↓

-T-C-G-A-T-5meC-G-A-T-5hmC-G-T-
-A-G-C-T-A-G————C-T-A-G————C-A-
(SEQ ID NO:11)

Hemi methylated

② Add DNMT1 to maintain 5meC

↓

(B) -T-C-G-A-T-5meC-G-A-T-5hmC-G-T-
-A-G-C-T-A-G-5meC-T-A-G————C-A-
(SEQ ID NO:12)

5hmC retained at parental strand only

Repeat 1 and 2 to dilute 5hmC

↓

Bisulfite sequencing of:  A) untreated (5meC + 5hmC)
                          B) treated (5meC)

➡  A − B = 5hmC

FIG. 5A
FIG. 5B
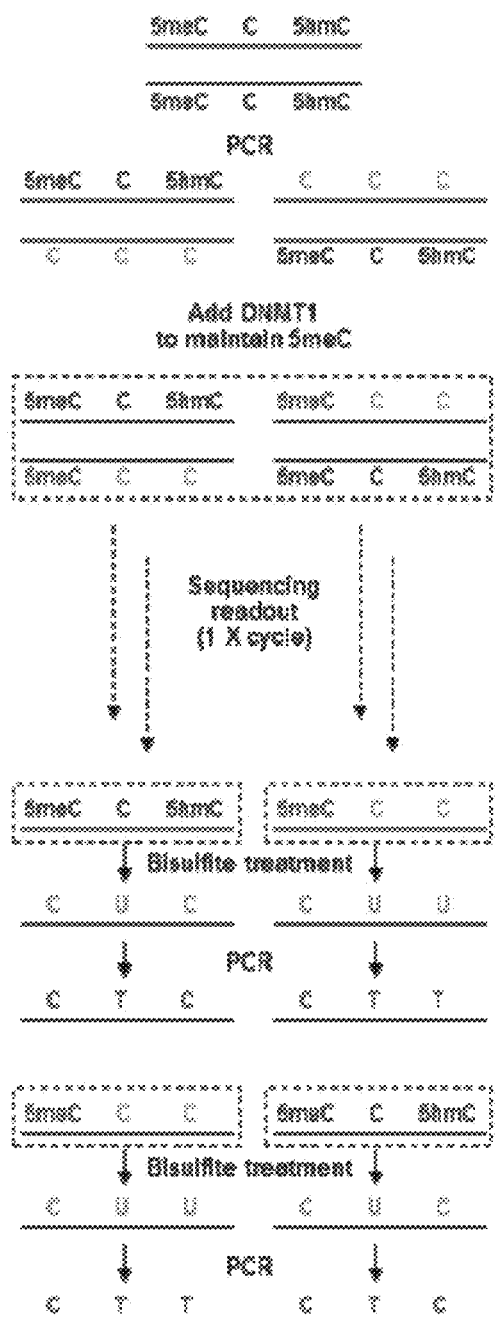
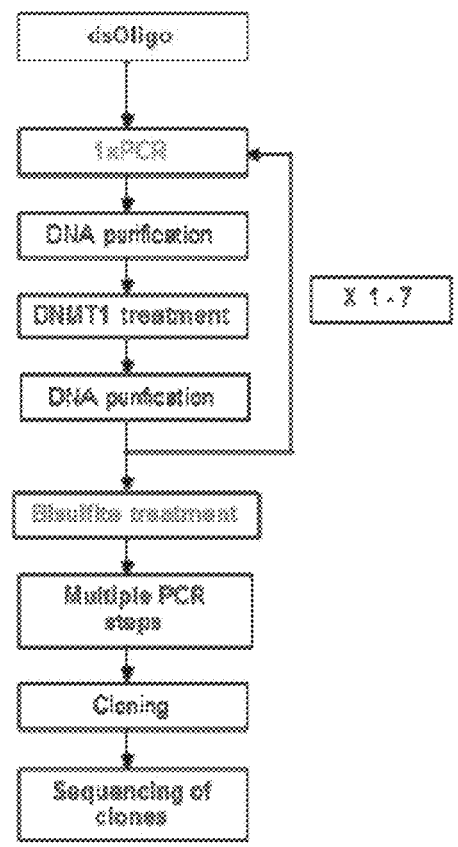

FIG. 6A
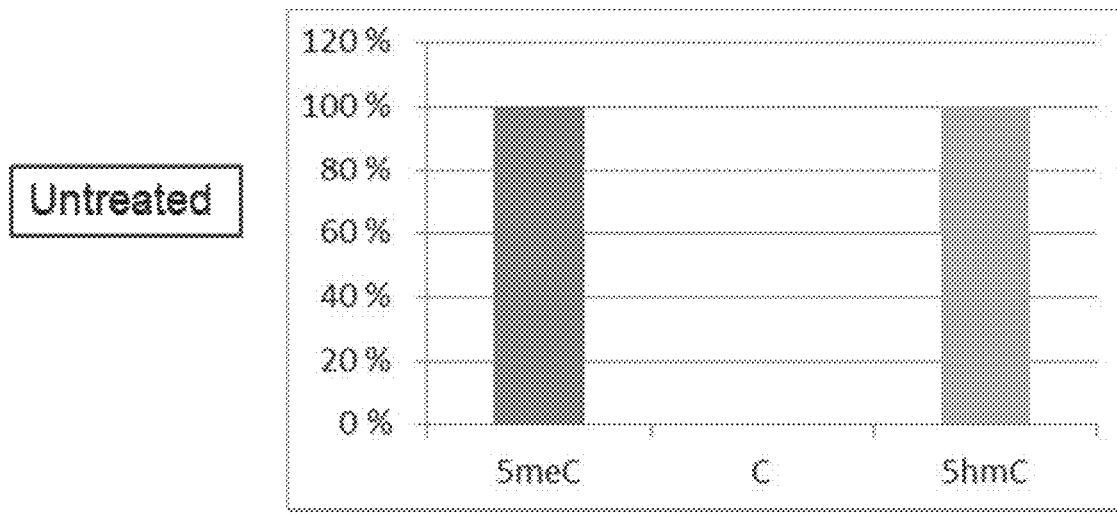
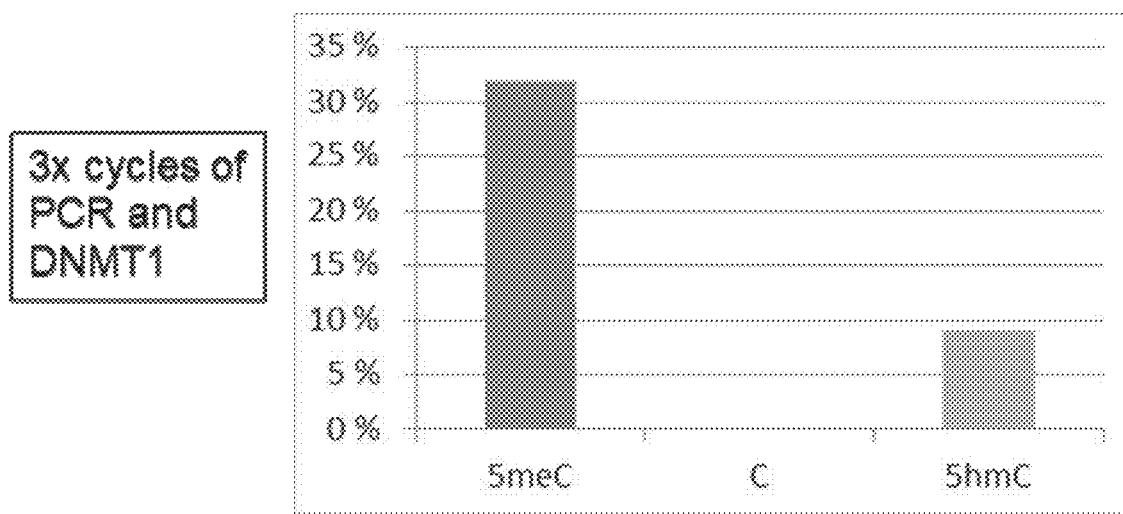
FIG. 6B

FIG. 8

DNMT1 (*Mus musculus*) Recombinant
Accession Number: GenBank: AAH53047.1

(Synonyms of gene name: Dnmt1; Dnmt; MCMT; Met1; Cxxc9; MTase; Met-1; Dnmt1o; m.MmuI; MommeD2).

MPARTAPARVPALASPAGSLPDHVRRRLKDLERDGLTEKECVREKLNLLHEFLQTEIKSQLCDLETKLHK
EELSEEGYLAKVKSLLNKDLSLENGTHTLTQKANGCPANGSRPTWRAEMADSNRSPRSRPKPRGPRRSKS
DSDTLCKDTRHTAVETSPSSVATRRTTRQTTITAHFTKGPTKRKPKEESEEGNSAESAAEERDQDKKRRV
VDTESGAAAAVEKLEEVTAGTQLGPEEPCEQEDDNRSLRRHTRELSLRRKSKEDPDREARPETHLDEDED
GKKDKRSSRPRSQPRDPAAKRRPKEAEPEQVAPETPEDRDEDEREEKRRKTTRKKLESHTVPVQSPSERK
AAQSKSVIPKINSPKCPECGQHLDDPNLKYQQHPEDAVDEPQMLTSEKLSIYDSTSTWFDTYEDSPMHRF
TSFSVYCSRGHLCPVDTGLIEKNVELYFSGCAKAIHDENPSMEGGINGKNLGPINQWWLSGFDGGEKVLI
GFSTAFAEYILMEPSKEYEPIFGLMQEKIYISKIVVEFLQNNPDAVYEDLINKIETTVPPSTINVNRFTE
DSLLRHAQFVVSQVESYDEAKDDDETPIFLSPCMRALIHLAGVSLGQRRATRRVMGATKEKDKAPTKATT
TKLVYQIFDTFFSEQIEKYDKEDKENAMKRRRCGVCEVCQQPECGKCKACKDMVKFGGTGRSKQACLKRR
CPNLAVKEADDDEEADDDVSEMPSPKKLHQGKKKKQNKDRISWLGQPMKIEENRTYYQKVSIDEEMLEVG
DCVSVIPDDSSKPLYLARVTALWEDKNGQMMFHAHWFCAGTDTVLGATSDPLELFLVGECENMQLSYIHS
KVKVIYKAPSENWAMEGGTDPETTLPGAEDGKTYFFQLWYNQEYARPESPPKTQPTEDNKHKFCLSCIRL
AELRQKEMPKVLEQIEEVDGRVYCSSITKNGVVYRLGDSVYLPPEAFTFNIKVASPVKRPKKDPVNETLY
PEHYRKYSDYIKGSNLDAPEPYRIGRIKEIHCGKKKGKVNEADIKLRLYKFYRPENTHRSYNGSYHTDIN
MLYWSDEEAVVNFSDVQGRCTVEYGEDLLESIQDYSQGGPDRFYFLEAYNSKTKNFEDPPNHARSPGNKG
KGKGKGKGKGKHQVSEPKEPEAAIKLPKLRTLDVFSGCGGLSEGFHQAGISETLWAIEMWDPAAQAFRLN
NPGTTVFTEDCNVLLKLVMAGEVTNSLGQRLPQKGDVEMLCGGPPCQGFSGMNRFNSRTYSKFKNSLVVS
FLSYCDYYRPRFFLLENVRNFVSYRPSMVLKLTLRCLVRMGYQCTFGVLQAGQYGVAQTRRRAIILAAAP
GEKLPLFPEPLHVFAPRACQLSVVVDDKKFVSNITRLSSGPFRTITVRDTMSDLPEIQNGASNSEIPYNG
EPLSWFQRQLRGSHYQPILRDHICKDMSPLVAARMRHIPLFPGSDWRDLPNIQVRLGDGVIAHKLQYTFH
DVKNGYSSTGALRGVCSCAEGKACDPESRQFSTLIPWCLPHTGNRHNHWAGLYGRLEWDGFFSTTVTNPE
PMGKQGRVLHPEQHRVVSVRECARSQGFPDSYRFFGNILDRHRQVGNAVPPPLAKAIGLEIKLCLLSSAR
ESASAAVKAKEEAATKD

FIG. 9

DNMT1 (*Homo sapiens*)
Accession Number: GenBank: AAI44094.1

MPARTAPARVPTLAVPAISLPDDVRRRLKDLERDSLTEKECVKEKLNLLHEFLQTEIKNQLCDLETKLRK
EELSEEGYLAKVKSLLNKDLSLENGAHAYNREVNGRLENGNQARSEARRVGMADANSPPKPLSKPRTPRR
SKSDGEAKRSRDPPASASQVTGIRAEPSPSPRITRKSTRQTTITSHFAKGPAKRKPQEESERAKSDESIK
EEDKDQDEKRRRVTSREPVARPLPAEEPERAKSGTRTEKEEERDEKEEKRLRSQTKEPTPKQKLKEEPDR
EARAGVQADEDEDGDEKDEKKHRSQPKDLAAKRRPEEKEPEKVNPQISDEKDEDEKEEKRRKTTPKEPTE
KKMARAKTVMNSKTHPPKCIQCGQYLDDPDLKYGQHPPDAVDEPQMLTNEKLSIFDANESGFESYEALPQ
HKLTCFSVYCKHGHLCPIDTGLIEKNIELFFSGSAKPIYDDDPSLEGGVNGKNLGPINEWWITGFDGGEK
ALIGFSTSFAEYILMDPSPEYAPIFGLMQEKIYISKIVVEFLQSNSDSTYEDLINKIETTVPPSGLNLNR
FTEDSLLRHAQFVVEQVESYDEAGDSDEQPIFLTPCMRDLIKLAGVTLGQRRAQAPRRQTIRHSTREKDRG
PTKATTTKLVYQIFDTFFAEQIEKDDREDKENAFKRRRCGVCEVCQQPECGKCKACKDMVKFGGSGRSKQ
ACQERRCPNMAMKEADDDEEVDDNIPEMPSPKKMHQGKKKKQNKNRISWVGEAVKTDGKKSYYKKVCIDA
ETLEVGDCVSVIPDDSSKPLYLARVTALWEDSSNGQMFHAHWFCAGTDTVLGATSDPLELFLVDECEDMQ
LSYIHSKVKVIYKAPSENWAMEGGMDPESLLEGDDGKTYFYQLWYDQDYARFESPPKTQPTEDNKFKFCV
SCARLAEMRQKEIPRVLEQLEDLDSRVLYYSATKNGILYRVGDGVYLPPEAFTFNIKLSSPVKRPRKEPV
DEDLYPEHYRKYSDYIKGSNLDAPEPYRIGRIKEIFCPKKSNGRPNETDIKIRVNKFYRPENTHKSTPAS
YHADINLLYWSDEEAVVDFKAVQGRCTVEYGEDLPECVQVYSMGGPNRFYFLEAYNAKSKSFEDPPNHAR
SPGNKGKGKGKGKGKPKSQACEPSEPEIEIKLPKLRTLDVFSGCGGLSEGFHQAGISDTLWAIEMWDPAA
QAFRLNNPGSTVFTEDCNILLKLVMAGETTNSRGQRLPQKGDVEMLCGGPPCQGFSGMNRFNSRTYSKFK
NSLVVSFLSYCDYYRPRFFLLENVRNFVSFKRSMVLKLTLRCLVRMGYQCTFGVLQAGQYGVAQTRRRAI
ILAAAPGEKLPLFPEPLHVFAPRACQLSVVVDDKKFVSNITRLSSGPFRTITVRDTMSDLPEVRNGASAL
EISYNGEPQSWFQRQLRGAQYQPILRDHICKDMSALVAARMRHIPLAPGSDWRDLPNIEVRLSDGTMARK
LRYTHHDRKNGRSSSGALRGVCSCVEAGKACDPAARQFNTLIPWCLPHTGNRHNHWAGLYGRLEWDGFFS
TTVTNPEPMGKQGRVLHPEQHRVVSVRECARSQGFPDTYRLFGNILDKHRQVGNAVPPPLAKAIGLEIKL
CMLAKARESASAKIKEEEAAKD

FIG. 10

M.SssI (Spiroplasmasp. (strain MQ1))
Site-specific DNA-methyltransferase (cytosine-specific) (EC 2.1.1.73) SssI - Spiroplasmasp. (strain MQ1)

```
  1 mskvenktkk lrvfeafagi gaqrkalekv rkdeyeivgl aewyvpaivm yqaihnnfht
 61 kleyksvsre emidylenkt lswnsknpvs ngywkrkkdd elkiiynaik lsekegnifd
121 irdlykrtlk nidlltysfp cqdlsqqgiq kgmkrgsgtr sgllweiera ldstekndlp
181 kyllmenvga llhkkneeel nqwkqklesl gyqnsievln aadfgssqar rrvfmistln
241 efvelpkgdk kpksikkvln kivsekdiln nllkynltef kktksninka sligyskfns
301 egyvydpeft gptltasgan srikikdgsn irkmnsdetf lyigfdsqdg krvneieflt
361 enqkifvcgn sisvevleai idkigg
```

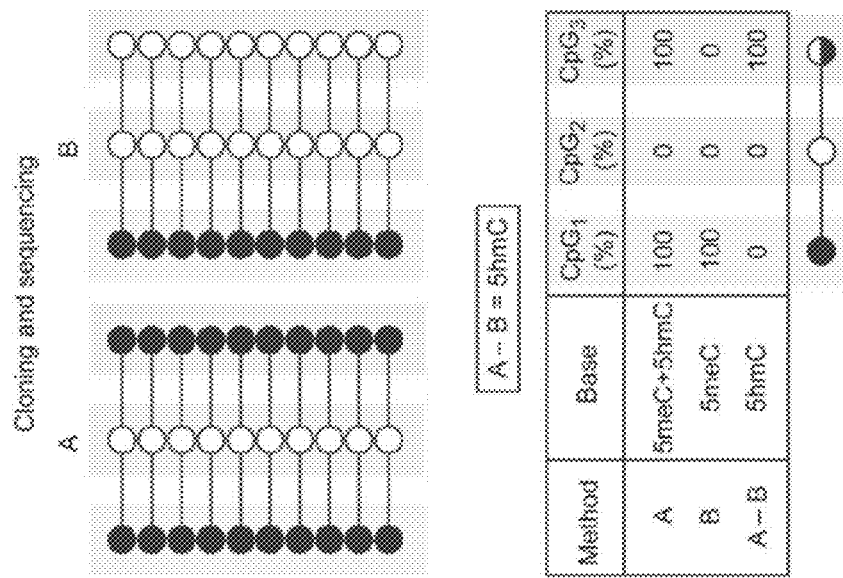
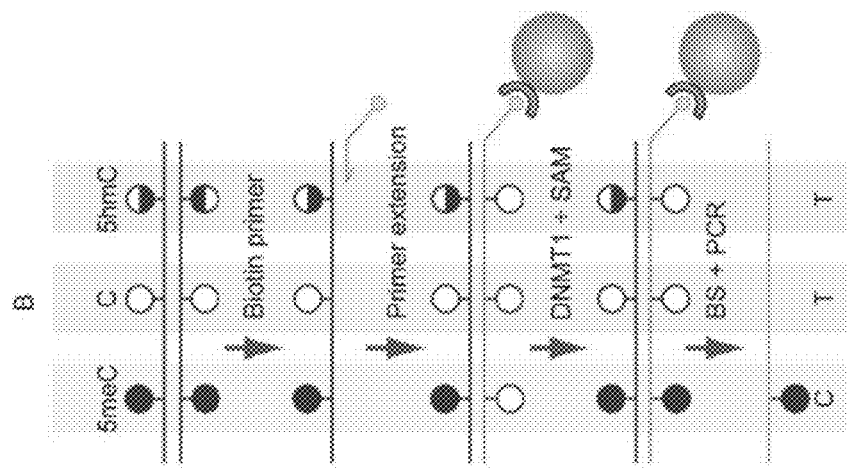
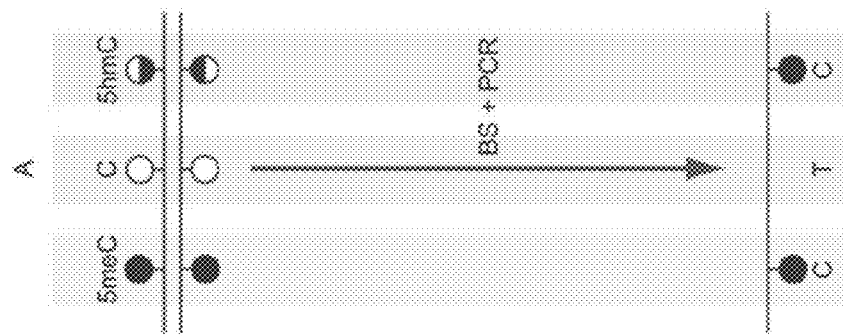
FIG. 11

METHODS AND KITS FOR DETECTION OF METHYLATION STATUS

CROSS-REFERENCE TO RELATED APPLICATIONS

This application is a continuation of U.S. patent application Ser. No. 14/363,442, filed Jun. 6, 2014, which is a 371 U.S. National Phase Entry of International Patent Application No. PCT/US2012/069525, International Filing Date Dec. 13, 2012, which claims priority to U.S. Provisional Patent Application No. 61/570,066, filed Dec. 13, 2011, the contents of which are incorporated by reference in their entireties.

SEQUENCE LISTING

The instant application contains a Sequence Listing which has been submitted electronically in ASCII format and is hereby incorporated by reference in its entirety. Said ASCII copy, created on Mar. 11, 2020, is named 32320-303_ST25.txt and is 35 kilobytes in size.

FIELD OF THE INVENTION

The present invention relates to methods and kits for the detection of 5-hydroxymethylcytosine (5hmC) and/or 5-methylcytosine (5meC). In some embodiments, the present invention relates to methods and kits for detection of 5hmC and/or 5meC in nucleic acid (e.g., DNA, RNA). In some embodiments, the present invention relates to detection of 5hmC in genomic DNA, e.g., mammalian genomic DNA.

BACKGROUND OF THE INVENTION

The 5-hydroxymethylcytosine (5hmC) modification in mammalian DNA was discovered over 30 years ago[1]. At that time the 5hmC modification was suggested to be a rare and non-mutagenic DNA damage lesion[2] and therefore it was given little attention. In early 2009 5hmC was identified again; however, in this year the importance of 5hmC in epigentics was realized as two independent groups began the initial characterization of the 5hmC modification. One group identified an enzyme capable of catalyzing the formation of 5hmC from 5-methylcytosin-Tet1[3]. The other group demonstrated that 5hmC was a stable modification present in specialized Purkinje neurons[4]. Further research has shown that Tet1, Tet2, and Tet3 are capable of catalyzing the oxidation of 5meC creating 5hmC[5-7].

The molecular function of 5hmC remains poorly understood; however, it has been shown that 5hmC is involved in a variety of DNA transactions: it has been shown to be an intermediate in DNA demethylation[3, 8], to have a dual function in transcription[9-11] and in the case of aberrant 5hmC patterns to be involved in tumorigenesis[7]. While the function of the 5hmC modification remains unclear, it has become clear that identifying genomic regions that contain 5hmC will help to elucidate the function of this base. This need to identify genomic regions containing 5hmC has led to the development of suitable methods. Currently, there are several methods available to identify 5hmC; each method has certain limitations that are discussed below. The method described here allows for base specific resolution of (i) 5hmC and (ii) 5meC in DNA.

Currently, there are several methods that allow for the identification of 5hmC. These methods include antibodies raised against 5hmC[9, 21, 22], antibodies raised against cytosine 5-methylenesulfonane (CMS) the product of bisulfite treatment of 5hmC[7, 23], single molecule real time sequencing relying on DNA polymerase kinetics[24], restriction enzymes that are resistant or sensitive to 5hmC or β-glu-5hmC[25-27] and three methods that take advantage of the β-glucosyltransferase: (i) incorporating a chemical tag into the substrate for the β-gt[28], (ii) the glucosylation, periodate oxidation, and biotinylation (GLIB) method[23], and (iii) the JBP1 pull-down assay targeting glu-5hmC[12]

The use of antibodies appears to be a reasonable choice to identify DNA modifications; however, we and others[5] have seen that some of the currently available antibodies directed against 5hmC appear to be unable to sufficiently enrich for DNA that contains 5hmC; indeed one report demonstrates that one particular antisera raised against 5hmC is unable to differentiate 5hmC from 5meC[5]. It has been reported that antisera developed against 5hmC tends to prefer genomic regions dense in 5hmC content[22]. Moreover, the use of polyclonal antisera directed against 5hmC will provide an inherent problem, as there will be animal-to-animal variation in antigenic specificity to 5hmC that may affect the long-term usefulness of such antisera.

Upon treatment with sodium bisulfite 5hmC is converted to CMS, which after sequencing appears identical to bisulfite converted 5meC; therefore it has been shown that the use of bisulfite sequencing cannot distinguish between 5meC and 5hmC[30]. Interestingly, one group has raised an antiserum directed against CMS[7, 23].

Single Molecule, Real Time (SMRT) sequencing takes advantage of the original Sanger sequencing technique; however, this method is able to distinguish between cytosine, 5meC, and 5hmC using the kinetic signature or speed that the polymerase passes over each base[24]. This method, aside from being prohibitively expensive, requires a significant amount of DNA that is already enriched for 5hmC prior to use, which makes it dependent on a 5hmC enrichment assay. Because this method uses high-throughput sequencing it is cumbersome for the analysis of single or a few loci.

Several research groups and companies have identified restriction enzymes that are sensitive or resistant to 5hmC or β-glu-5hmC[25-27]. The principle behind these systems is that upon treatment with the restriction enzymes unmodified DNA is cleaved, resulting in reduced signal in a qPCR reaction. This reduction in signal is then compared to an undigested sample and the difference in qPCR signals is proportional to the amount of 5hmC present in the initial sample. These methods work quite well for genomic regions that contain significant amounts of 5hmC; however, because the restriction sites recognized by these enzymes are 4-6 bp in length these restriction endonuclease based methods can, at best, only recognize ¹⁄₁₆ of all 5hmC modifications.

Three groups have developed methods that take advantage of the specificity that the β-gt has for 5hmC. The first group[28] incorporated an azide group into the substrate for the β-gt—UDP-glucose—creating UDP-6-$N_3$-Glucose. After the azide modified glucose was incorporated into 5hmC containing DNA by the β-gt, a second group could be added to the 6-$N_3$-glu-5hmC using "click" chemistry. This second chemical group could contain a biotin for pull down, a fluorescent probe for quantification, and theoretically any group that could be coupled to the modified glucose using "click" chemistry. The primary drawback to this method is that UDP-6-$N_3$-glucose is not commercially produced and requires significant expertise in organic chemistry to synthesize. Additionally, this targeting strategy of 5hmC has been combined with a primer extension assay and shown to allow for base specific resolution as a chemical group can be linked to 6-$N_3$-glu-5hmC that blocks a DNA polymerase. By blocking the polymerase the terminal base can be assumed to have originally contained a 5hmC modification. The use of this method for base specific resolution has substantial problems as every end that terminates in a C must be assumed to be a 5hmC. While this effect can potentially be averaged with several high throughput sequencing reads assuming highly optimized enzyme to DNA ratios, it remains problematical for single gene analysis.

A second approach using the β-gt to identify genomic regions uses the glucosylation, periodate oxidation, biotinylation (GLIB) method[23]. In this method after the transfer of glucose to 5hmC, the resulting β-glu-5hmC is oxidized using $NaIO_4$ which creates reactive aldehydes on the glucose moiety attached to 5hmC. These oxidized glucose molecules can then be reacted with commercially available aldehyde reactive probes containing a biotin modification. This biotinylation allows for the efficient pull down of 5hmC containing DNA.

Finally, the third approach utilizing the β-gt for the identification of 5hmC involves the specific recognition of this modified base by a second protein—J-base binding protein or JBP1. Because the only difference between β-glucosyl-5hmC and the J-base is an amino group, it was reasoned that JBP1 may be able to specifically interact with β-glu-5hmC. JBP1 was indeed able to specifically interact with β-glu-5hmC[12]. Therefore, when JBP1 was covalently linked to epoxy modified magnetic beads it allowed for the pull down of the β-glu-5hmC containing DNA. After removing protein from the pulled down DNA it was demonstrated by gene specific qPCR that it was possible to enrich for DNA containing 5hmC[12]. Mechanistically, this method provides two degrees of specificity for the identification of 5hmC in genomic DNA: first, the β-gt can only modify cytosines in DNA that are hydroxymethylated and second, JBP1 interacts specifically with β-glu-5hmC. Like all DNA pull down methods the very optimal resolution of this method can identify a 5hmC base within about 50-100 base pairs; this limitation is due to the inability to reliably identify DNA fragments of a shorter length using currently available molecular biology methods. Another consideration when using this protocol is that this method may over-represent DNA regions that contain high levels of 5hmC. This potential over-representation could possibly occur because in 5hmC dense regions more JBP1 can interact with the DNA and pull down these regions more efficiently.

Improved methods for detecting 5-hydroxymethylcytosine residues in DNA are needed. In particular, methods that can discriminate between 5meC and 5hmC are needed, as well as methods which can identify 5meC and 5hmC at single base resolution.

SUMMARY OF THE INVENTION

The present invention relates to methods and kits for the detection of 5-hydroxymethylcytosine (5hmC) and/or 5-methylcytosine (5meC). In some embodiments, the present invention relates to methods and kits for detection of 5hmC and/or 5meC in nucleic acid (e.g., DNA, RNA). In some embodiments, the present invention relates to detection of 5hmC in genomic DNA, e.g., mammalian genomic DNA.

In some embodiments, the present invention provides processes for detecting 5-methylated and/or other modified cytosine residues in a nucleic acid sample comprising: replicating said nucleic acid sample under conditions such that 5-methylated cytosine residues are maintained and said other modified cytosine residues are diluted; treating said replicated nucleic acid sample to convert unmodified cytosine residues to a uracil or thymidine residues; and reading the sequence of said replicated nucleic acid sample wherein 5-hydroxymethylated cytosine residues are identified as residues that are read by sequencing as a thymidine or uracil residue in said replicated nucleic acid sample. In some embodiments, the nucleic acid sample is divided into at least first and second portions and said replicating and treating steps are performed on said first portion, and comparing the sequence of said first nucleic acid portion with the sequence of said second nucleic acid portion, wherein said other modified cytosine residues are identified as residues that are read by sequencing as a uracil or thymidine residue in said first nucleic acid portion and as a cytosine residue at the corresponding position in said second nucleic acid portion and wherein 5-methylated cytosine residues are identified as residues that are read as cytosine residues in both of said first and second nucleic acid portions. In some embodiments, the replication of said first portion further comprises: a) replicating said nucleic acid with a tagged primer to provide tagged replicated nucleic acid; b) treating said tagged replicated nucleic acid strands with a DNA methyltransferase to provide tagged 5-methylcytosine-modified replicated nucleic acid; c) isolating said tagged 5-methylcytosine-modified replicated nucleic acid; d) treating said isolated tagged 5-methylcytosine-modified replicated nucleic acid with bisulfite to convert unmodified cytosine residues to uracil residues; and e) replicating said isolated tagged bisulfite-treated nucleic acid with a polymerase to provide a first bisulfite treated nucleic acid portion. In some embodiments, the tagged primer is a biotinylated primer. In some embodiments, the other modified cytosine residues are selected from the group consisting of 5-hydroxymethyl cytosine, beta-glu-5-hydroxymethyl cytosine, alpha-glucosyl-5-hydroxymethylcytosine, beta-glucopyranosyl-alpha-glycosyl-5-hydroxymethylcytosine (gentiobiosyl-5-hydroxymethylcytosine), 5-formylcytosine and 5-carboxycytosine.

In some embodiments, the replicating said first portion under conditions such that 5-methylated cytosine residues are maintained and 5-hydroxymethylated cytosine residues are diluted comprises replicating said nucleic acid with a polymerase to provide replicated nucleic acid and treating said replicated nucleic acid with an enzyme to 5-methylate cytosine residues. In some embodiments, the steps of replication and treating with an enzyme are performed one or more times. In some embodiments, the steps of replication and treating with an enzyme are repeated 5 or more times. In some embodiments, the steps of replication and treating with an enzyme are repeated 7 or more times. In some embodiments, the steps of replication and treating with an enzyme are repeated 10 or more times. In some embodiments, the steps of replication and treating with an enzyme are performed from about 1 to about 20 times or more. In some embodiments, replication is by a polymerase chain reaction. In some embodiments, replication is by a primer extension reaction. In some embodiments, the enzyme is a DNA methyltransferase. In some embodiments, the DNA methyltransferase is DNMT1. In some embodiments, the DNA methyltransferase is M.Sss1.

In some embodiments, the treating said first and second portions to convert unmodified cytosine residues to thymidine residues further comprises treating said first and second nucleic acid portions with bisulfite to convert unmodified cytosine residues to uracil resides and replicating said first and second nucleic acid portions with a polymerase to convert said uracil residues into thymidine residues. In some embodiments, replication is performed 1 or more times. In some embodiments, replication is performed 5 or more times. In some embodiments, replication is performed 7 or more times. In some embodiments, replication is performed 10 or more times. In some embodiments, replication is repeated from about 1 to about 20 times. In some embodiments, the replication is by a polymerase chain reaction. In some embodiments, the replication is by a primer extension reaction.

In some embodiments, the nucleic acid sample is selected from the group consisting of human, plant, mouse, rabbit, hamster, primate, fish, bird, cow, sheep, pig, viral, bacterial and fungal nucleic acid samples.

In some embodiments, the processes further comprise comparing the presence of 5-hydroxymethylcytosine and/or 5-methylcytosine in said nucleic acid in said sample to a reference standard, wherein an increased or decreased level of 5-hydroxymethylcytosine and/or 5-methylcytosine in said nucleic acid is indicative of the presence of a disease or of the probable course of a disease. In some embodiments, the processes further comprise the step of providing a diagnoses or prognoses based on an increased or decreased level of 5-hydroxymethylcytosine and/or 5-methylcytosine in said nucleic acid as compared to a reference standard. In some embodiments, the disease is cancer. In some embodiments, the nucleic acid sample is genomic DNA.

In some embodiments, the present invention provides processes for detecting methylated and hydroxymethylated cytosine residues in a nucleic acid sample comprising: a) dividing said sample into at least first and second untreated portions; b) replicating said first portion with a tagged primer and a polymerase to provide parent and tagged replicated nucleic acid; c) treating said parent and said tagged replicated nucleic acid strands with a DNA methyltransferase to provide tagged 5-methylcytosine-modified replicated nucleic acid; d) isolating said tagged 5-methylcytosine-modified replicated nucleic acid; e) treating said isolated tagged 5-methylcytosine-modified replicated nucleic acid with bisulfite to convert unmodified cytosine residues to uracil residues; f) replicating said isolated tagged bisulfite-treated nucleic acid with a polymerase to provide a first bisulfite treated nucleic acid portion; g) sequencing said first bisulfite treated nucleic acid portion; h) treating said second portion with bisulfite to convert unmodified cytosine residues to uracil residues; i) replicating said bisulfite-treated nucleic acid with a polymerase to provide a second bisulfite treated nucleic acid portion; j) sequencing said second bisulfite treated nucleic acid portion; and k) comparing the sequence of said first bisulfite treated nucleic acid portion with the sequence of said second bisulfite treated portion, wherein 5-hydroxymethylated cytosine residues are identified as residues that are read by sequencing as a uracil or thymidine residue in said first bisulfite treated nucleic acid portion and as a cytosine residue at the corresponding position in said second bisulfite treated nucleic acid portion and wherein 5-methylated cytosine residues are identified as residues that are read as cytosine residues in said first and second bisulfite treated portions. In some embodiments, said second portion is replicated with a polymerase prior to said sequencing step. In some embodiments, said steps b, c and d are repeated from about 2 to about 20 times. In some embodiments, said steps e and h are repeated from about 2 to about 20 times. In some embodiments, said replicating in steps b, e and h is by polymerase chain reaction. In some embodiments, the processes further comprise comparing the presence of 5-hydroxymethylcytosine and/or 5-methylcytosine in said nucleic acid in said sample to a reference standard, wherein an increased or decreased level of 5-hydroxymethylcytosine and/or 5-methylcytosine in said nucleic acid is indicative of the presence of a disease or of the probable course of a disease. In some embodiments, the processes further comprise the step of providing a diagnoses or prognoses based on an increased or decreased level of 5-hydroxymethylcytosine and/or 5-methylcytosine in said nucleic acid as compared to a reference standard. In some embodiments, the disease is cancer. In some embodiments, the nucleic acid sample is genomic DNA.

In some embodiments, the present invention provides a process for predicting a predisposition to as disease in a subject, diagnosing a disease in a subject, predicting the likelihood of recurrence of disease in a subject, providing a prognosis for a subject with a disease, or selecting a subject with a disease for treatment with a particular therapy, comprising: a) providing a genomic DNA sample from said subject; and b) detecting the methylation status of predetermined portions of said genomic DNA sample by the processes described above, wherein an altered level of 5-hydroxymethylcytosine and/or 5-methylcytosine methylation of said predetermined portions of said genomic DNA to a reference methylation status provides an indication selected from the group consisting of an indication of a predisposition of the subject to a disease, an indication that the subject has a disease, an indication of the likelihood of recurrence of a disease in the subject, an indication of survival of the subject, and an indication that the subject is a candidate for treatment with a particular therapy. In some embodiments, the disease is a cancer. In some embodiments, the subject is a human.

In some embodiments, the present invention provides a kit for determination of the methylation status of a nucleic acid sample comprising: 1) container(s) with reagents for methylating nucleic acid; and 2) container(s) with reagents for bisulfite sequencing. In some embodiments, the kits further comprise nucleic acid primers for amplifying and/or sequencing a region of said nucleic acid sample. In some embodiments, the kits further comprise a computer readable medium comprising a computer algorithm that analyzes sequence data obtained using said kit.

Additional embodiments will be apparent to persons skilled in the relevant art based on the teachings contained herein.

DESCRIPTION OF THE DRAWINGS

FIG. 5A-B. Schematic presentation of the method for distinct identification of 5hmC and 5meC at base specific resolution. (A) A scheme following the C bases of the CpG sites of a dsDNA oligo which contains three CpG sites where one is having 5meC at both strands, a second one is having no modification and a third one is having 5hmC at both strands. The CpG sites are followed through one round of PCR (melting, primer annealing and elongation) and DNMT1 treatment before visualization of bisulfite treatment and PCR (30 cycles) which generates the bases that will be read in the sequencing. (B) Flow chart of the experimental procedure involved in the 5hmC dilution assay.

FIG. 6A-B. Preferential maintenance of 5meC over 5hmC. The double stranded DNA oligo used here contains three CpG sites, one having 5meC at both strands, a second one having no modification and a third one having 5hmC at both strands. (A) Bisulfite conversion and sequencing of the untreated oligo showed that only modified Cs were protected from being converted (100% for both 5meC and 5hmC), whereas unmodified cytosines were all converted. (B) Taking the double stranded DNA oligo through three rounds of the dilution assay, involving PCR and treatment with DNMT1, prior to bisulfite conversion and sequencing resulted in preferential maintenance of 5meC over 5hmC. There was no methylation across from 5hmC in any of the three rounds as the initial 5hmC modified strands made up only 9% of the total pool after three rounds of the dilution assay. (One would expect 50% after one round, 25% after two rounds and 12.5% after three rounds when there is no maintenance at all). The 5meC base was preferentially maintained, thus resulted in a higher number of Cs protected in the bisulfite conversion and a significantly higher read out than the 5hmC base. No addition of a methyl group was observed across from either C or 5hmC.

FIG. 8. Amino acid sequence for DNMT1 (Mus musculus) Recombinant Accession Number: GenBank: AAH53047.1 (SEQ ID NO:1).

FIG. 9. Amino acid sequence for DNMT1 (Homo sapiens) Accession Number: GenBank: AAI44094.1 (SEQ ID NO:2).

FIG. 10. Amino acid sequence for M.Sss1 (*Spiroplasma* sp. (strain MQ1)) site-specific DNA-methyltransferase (SEQ ID NO:3).

FIG. 11. Schematic depiction of of a 5hmC loss assay of the present invention utilizing biotinylated primers and streptavidin capture beads. Right panel, top, shows representative sequencing results of 10 clones for the conventional bisulfite assay, referred to as A, where both 5meC and 5hmC will be read as cytosine after treatment, and sequencing results of 10 clones for the methyl transfer assay/5hmC loss assay, referred to as B, where only 5meC will be read as cytosine after treatment. Cytosines in a CG sequence context (CpG) protected from bisulfite conversion are illustrated as filled circles whereas cytosines in a CG sequence context which undergo deamination to Uracil in the bisulfite treatment are illustrated as open circles. The combination of the standard bisulfite assay data, A, where both 5meC and 5hmC will be read as cytosine after treatment and the methyl transfer assay, B, where only 5meC will be read as a cytosine after treatment allows for determination of position and quantity of 5hmC, from the simple calculation: A-B=5hmC. This quantification is outlined in the bottom of the right panel. These experimental results have been reproduced in 15 independent experiments.

DEFINITIONS

Figure 1:
FIG. 1. Schematic depiction of certain embodiments of the present invention, which applies bisulfite conversion and sequencing of "A" untreated DNA which will be used as a reference as it will detect the total of both 5meC and 5hmC. The method involves a 5hmC dilution assay, diluting 5hmC in the total pool of DNA fragments while maintaining 5meC. This dilution is achieved through sequential rounds of one cycle of PCR amplification (dilution) and treatment of the DNA with the DNA maintenance methyltransferase DNMT1 which enzymatically and specifically maintains 5meC by adding a methyl group uniquely to the unmethylated strand of the hemimethylated PCR products (this sample is referred to as "B" in FIG. 1). After a few rounds of this assay we apply bisulfite conversion and sequencing of the treated DNA sample, B. Bases that read as cytosine from this sample must have been protected against bisulfite conversion because of 5meC and not 5hmC. By comparing "B" to the reference sample "A" we can easily detect all base positions containing 5hmC.

To facilitate an understanding of the present invention, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (e.g., epigenetic marker; e.g., 5hmC at one or more particular locations) in a positive sample.

As used herein, the term "dilution" refers to the reduction of non-5-methyl modified cytosine residues (e.g., 5-hydroxymethl cytosine residues) in a nucleic acid sample as compared to the 5-methyl cytosine residues through repeated rounds of replication of said DNA sample.

As used herein the term "non-5-methyl cytosine modified cytosine residues" refers to modified cytosine residues other than 5-methyl cytosine, for example, 5-hydroxymethyl cytosine, b-glu-5-hydroxymethyl cytosine, 5-formyl-cytosine and 5-carboxycytosine.

As used herein, the term "CpG island" refers to a genomic DNA region that contains a high percentage of CpG sites relative to the average genomic CpG incidence (per same species, per same individual, or per subpopulation (e.g., strain, ethnic subpopulation, or the like). Various parameters and definitions for CpG islands exist; for example, in some embodiments, CpG islands are defined as having a GC percentage that is greater than 50% and with an observed/expected CpG ratio that is greater than 60% (Gardiner-Garden et al. (1987) J Mol. Biol. 196:261-282; Baylin et al. (2006) Nat. Rev. Cancer 6:107-116; Irizarry et al. (2009) Nat. Genetics 41:178-186; each herein incorporated by reference in its entirety). In some embodiments, CpG islands may have a GC content >55% and observed CpG/expected CpG of 0.65 (Takai et al. (2007) PNAS 99:3740-3745; herein incorporated by reference in its entirety). Various parameters also exist regarding the length of CpG islands. As used herein, CpG islands may be less than 100 bp; 100-200 bp, 200-300 bp, 300-500 bp, 500-750 bp; 750-1000 bp; 1000 or more bp in length. In some embodiments, CpG islands show altered methylation patterns (e.g., altered 5hmC patterns) relative to controls (e.g., altered 5hmC methylation in cancer subjects relative to subjects without cancer; tissue-specific altered 5hmC patterns; altered 5hmC patterns in biological samples from subjects with a neoplasia or tumor relative to subjects without a neoplasia or tumor. In some embodiments, altered methylation involves increased incidence of 5hmC. In some embodiments, altered methylation involves decreased incidence of 5hmC.

As used herein, the term "CpG shore" or "CpG island shore" refers to a genomic region external to a CpG island that is or that has potential to have altered methylation (e.g., 5hmC) patterns (see, e.g., Irizarry et al. (2009) Nat. Genetics 41:178-186; herein incorporated by reference in its entirety). CpG island shores may show altered methylation (e.g., 5hmC) patterns relative to controls (e.g., altered 5hmC in cancer subjects relative to subjects without cancer; tissue-specific altered 5hmC patterns; altered 5hmC in biological samples from subjects with neoplasia or tumor relative to subjects without neoplasia or tumor. In some embodiments, altered methylation involves increased incidence of 5hmC. In some embodiments, altered methylation involves decreased incidence of 5hmC. CpG island shores may be located in various regions relative to CpG islands (see, e.g., Irizarry et al. (2009) Nat. Genetics 41; 178-186; herein incorporated by reference in its entirety). Accordingly, in some embodiments, CpG island shores are located less than 100 bp; 100-250 bp; 250-500 bp; 500-1000 bp; 1000-1500 bp; 1500-2000 bp; 2000-3000 bp; 3000 bp or more away from a CpG island.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body.

As used herein, "an individual is suspected of being susceptible to metastasized cancer" is meant to refer to an individual who is at an above-average risk of developing metastasized cancer. Examples of individuals at a particular risk of developing cancer of a particular type (e.g., colorectal cancer, bladder cancer, breast cancer, prostate cancer) are those whose family medical history indicates above average incidence of such cancer type among family members and/or those who have already developed cancer and have been effectively treated who therefore face a risk of relapse and recurrence. Other factors which may contribute to an above-average risk of developing metastasized cancer which would thereby lead to the classification of an individual as being suspected of being susceptible to metastasized cancer may be based upon an individual's specific genetic, medical and/or behavioral background and characteristics.

The term "neoplasm" as used herein refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells.

As used herein, the term "amplicon" refers to a nucleic acid generated using primer pairs. The amplicon is typically single-stranded DNA (e.g., the result of asymmetric amplification), however, it may be RNA or dsDNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specfic PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, etl al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, 5-hydroxymethylcytosine, b-glucosyl-5-hydroxymethylcytosine, 5-formylcytosine, and 5-carboxycytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

DETAILED DESCRIPTION OF THE INVENTION

The present invention relates to methods and kits for the detection of 5-hydroxymethylcytosine (5hmC) and/or 5-methylcytosine (5meC). In some embodiments, the present invention relates to methods and kits for detection of 5hmC and/or 5meC in nucleic acid (e.g., DNA, RNA). In some embodiments, the present invention relates to detection of 5hmC in genomic DNA, e.g., mammalian genomic DNA. Current methods available for identifying 5hmC have a resolution limit of about 50-200 base pairs. Many of the current methods are limited by the step of bisulfate conversion which cannot distinguish between 5-methylcytosine (5meC) and 5hmC. The present invention addresses both of these problems. First, the present invention allows for discrimination between 5meC and 5hmC DNA modifications. Second, the present invention allows for the detection of both 5meC and 5hmC at single base resolution.

The method described here identifies 5-hydroxymethylcytosine (5hmC) in DNA with single base resolution. Additionally, this method can identify 5meC at base specific resolution concurrently with 5hmC. The method employed takes advantage of the fact that the DNMT1 methyltransferase cannot methylate across from a 5hmC (or modified 5hmC; as is the case for β-glucosyl-5-hydroxymethylcytosine) and preferentially methylates across from 5-methylcytosine (5meC). After sequential rounds of one cycle of PCR amplification and treatment of the DNA with DNMT1 the population of DNAs containing 5hmC is diluted by a factor of two whereas the population containing 5meC remains stable. This dilution coupled with bisulfite conversion allows for the base specific identification of DNA residues that contain 5hmC (FIG. 1).

Figure 2:
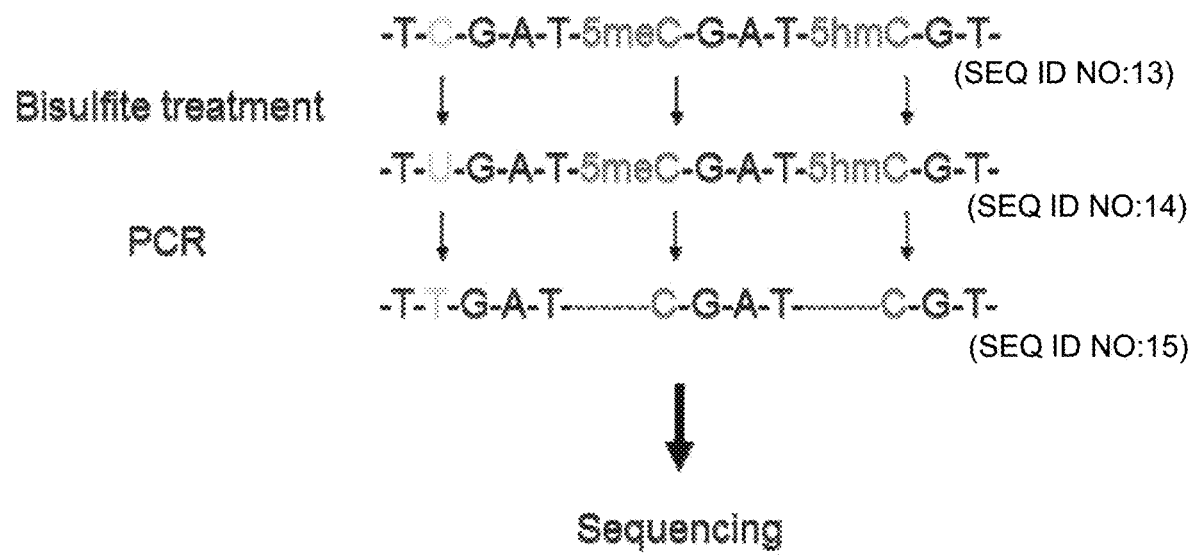
FIG. 2. Bisulfite conversion of DNA results in conversion of unmodified cytosine (C) to uracil (U) that will be read as thymine (T) upon sequencing of PCR amplified DNA. Both 5meC and 5hmC are protected against conversion and will not be converted to U. Therefore, both bases will be read as C upon sequencing. Bisulfite conversion is a well established technology that has long been regarded as the gold standard for detection of 5meC, and it was not until recently (2010) that it was reported in the scientific literature that bisulfite conversion can not distinguish between 5meC and 5hmC.

Bisulfite conversion of DNA results in conversion of unmodified cytosine (C) to uracil (U) that will be read as thymine (T) upon sequencing of PCR amplified DNA. Both 5meC and 5hmC are protected against conversion and will not be converted to U. Therefore they will both be read as C upon sequencing (see FIG. 2). Bisulfite conversion is a well established technology that has long been regarded as the gold standard for detection of 5meC, and it was not until recently (2010) that it was reported in the scientific literature that it cannot distinguish between 5meC and 5hmC[30]. However, the method described here takes advantage of this fact to create a reference data set (referred to as "A" in FIG. 1).

In preferred embodiments of the present invention, 5hmC is diluted in the total pool of DNA while maintaining 5meC. This dilution is achieved through sequential rounds of one cycle of PCR amplification and treatment of the DNA with the DNA maintenance methyltransferase DNMT1 which enzymatically and specifically maintains 5meC only by adding a methyl group to the unmethylated strand of the hemimethylated PCR products (this sample is referred to as "B" in FIG. 1). After one or more rounds of this assay, bisulfite conversion is performed followed by sequencing of the treated DNA sample, where 5meC now is the predominant modification. It is contemplated that all or most bases read as C from this sample must have been protected against conversion because of 5meC and not 5hmC. By comparing to the reference sample "A" it is possible to detect all base positions containing 5hmC. The dilution may be achieved on a genome wide basis or with respect to a particular gene locus or portion of a gene. In preferred embodiments, the region of dilution is defined by primers utilized for replication and/or amplification of a target region of interest.

Accordingly, in some embodiments, the present invention provides processes for detecting or determining the 5meC and/or 5hmC status of a nucleic acid sample, and in particularly preferred embodiments, the 5meC and/or 5hmC status or a predetermined region of a genomic DNA sample. In some preferred embodiments, the predetermined region (or target region of interest) corresponds to a gene locus of interest, or to a portion of a gene. In some embodiments, the predetermined region is defined by nucleic acid primers utilized for replication or amplification of the predetermined region.

In some preferred embodiments, the nucleic acid sample is divided into at least two portions for further analysis. In some embodiments, the first portion is replicated under conditions such that 5-methylated cytosine residues are maintained and 5-hydroxymethylated cytosine residues are diluted. The present invention is not limited to any particular level of dilution. For example, the 5-hydroxymethylated cytosine residues may be diluted by a factor of 1.5, 2, 5, 10, 20, 40, 100, 200, 400, 800, 1600 or more.

Figure 7A:
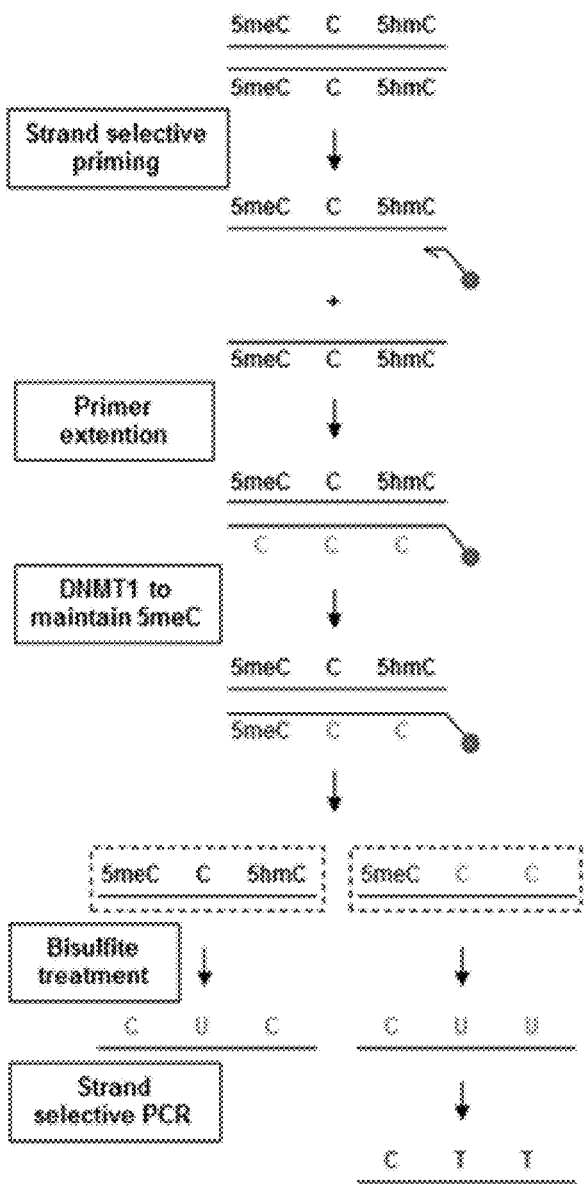
FIG. 7A-B. Schematic presentation of the method for distinct identification of 5hmC and 5meC at base specific resolution making use of strand specific assessment. (A) A scheme following the C bases of the CpG sites of a dsDNA oligo which contains three CpG sites where one is having 5meC at both strands, a second one is having no modification and a third one is having 5hmC at both strands. The CpG sites are followed through one round of strand specific primer extension PCR (melting, primer annealing and elongation) and DNMT1 treatment. The primer used may contain a biotin tag, or other tag, to allow for selection/isolation of the newly synthesized strand. The newly synthesized strand undergoes bisulfite treatment and PCR (30 cycles or other number) which generates the bases that will be read in the sequencing. (B) Flow chart of the experimental procedure involved in the 5hmC dilution/loss assay applying primer extension and strand specific assessment.
Figure 7B:
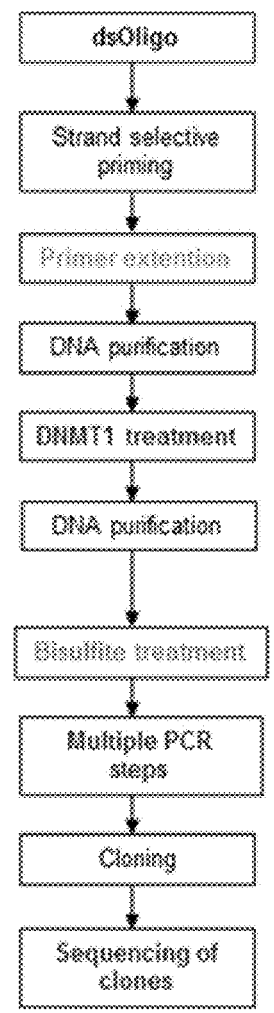

In some embodiments, the dilution of 5-hydroxymethylated cytosine residues is accomplished by replicating the nucleic acid (preferably replicating the predetermined region) with a polymerase to provide replicated nucleic acid and then treating the replicated nucleic acid with an enzyme that adds a methyl group to the unmethylated strand of the hemimethylated nucleic acid, but that does not add a hydroxymethyl group to the unhydroxymethylated strand of hemihydroxymethylated nucleic acid. The present invention is not limited to the use of any particular enzyme. In some embodiments, the enzyme is an enzyme that maintains the DNA methylation status of a nucleic acid, for example a DNA methyltransferase (DNMT). Example of DNA methyltransferases include, but are not limited to, mouse DNMT1 (SEQ ID NO:1; FIG. 7), human DNMT1 (SEQ ID NO:2, FIG. 8) or M.SssI (*Spiroplasma* sp.) DNMT (SEQ ID NO:3, FIG. 9), or a homolog or variant thereof. In some embodiments, the homologs or variants have the activity of adding a methyl group to the unmethylated strand of a hemimethylated nucleic acid. In some embodiments, the homologs or variants have at least 50%, 60%, 70%, 80%, 90%, 95%, or 99% identity to SEQ ID NOs:1, 2 or 3 and/or have the activity of adding a methyl group to the unmethylated strand of a hemimethylated nucleic acid.

In some embodiments, the replication step is performed via one or more rounds of polymerase chain reaction. In preferred embodiments, a predetermined region is replicated by extension from nucleic acid primers defining the 5' and 3' boundaries of the predetermined region. The replicated nucleic acid is then treated with a DNA methylation enzyme as described above to maintain 5-methylcytosine methylation of the predetermined region and then the process is repeated until a desired level of dilution of 5-hydroxymethylated cytosine residues as compared to 5-methylated residues is achieved. In some embodiments, the level of dilution per cycle is preferably about 2 fold, but may be as low as 1.1. In some embodiments, the level of maintenance of 5-methyl cytosine residues is about 100%, but may be as low as 10% and still provide effective determination of and discrimination between 5meC and 5hmC residues in the predetermined region. In some embodiments, the number of cycles of replication and treatment with DNA methylation enzyme may 1, 2, 3, 5, 7, 10 or 20 cycles or more, or between about 1 and 20 cycles.

In some embodiments, tagged primers are used in the replication step so that tagged extension products from the replication step may be isolated using a tag binding reagent and used in subsequent steps, such as for treatment with a DNA methyltransferase. In preferred embodiments, only the newly synthesized stands (i.e., strands tagged by the tagged primer) are used and analyzed in the subsequent steps. FIG. 11 provides a schematic depiction of the use of tagged primers in the process. In this figure, "A" shows the conventional bisulfite conversion and sequencing assay and "B" shows the methyl transferase dependent assay. As shown in the left panel for assay "B", the use of primer extension from a biotinylated primer and subsequent isolation with streptavidin beads ensures that all bottom strands in the analysis will be of the newly synthesized ones. Therefore, by performing DNMT1 (or other methyl transferase) treatment and next analyze the biotin-streptavidin isolated bottom strands one will get a direct and accurate quantification of the 5meC level of the complementary strand. Right panel, top, shows representative sequencing results of 10 clones for the standard bisulfite assay, "A", where both 5meC and 5hmC will be read as cytosine after treatment, and representative sequencing results of 10 clones for the methyl transfer assay "B" where only 5meC will be read as a cytosine after treatment. The combination of the standard bisulfite assay data, "A", where both 5meC and 5hmC will be read as cytosine after treatment and the methyl transfer assay "B" where only 5meC will be read as a cytosine after treatment allows for determination of position and quantity of 5hmC (from the simple calculation: A-B=5hmC). This quantification is outlined in the bottom of the right panel. For experimental replicates with this exact quantitative outcome we have n=15.

The present invention is not limited to the use of any particular tagged primer or tag binding reagent for isolation of the tagged primer. In some preferred embodiments, the primer is biotinylated and the tag binding reagent is a streptavidin reagent, such as a streptavidin bead. Replicated nucleic acid strands comprising the biotinylated primer (i.e., the primer extension product resulting from extension of the biotinylated primer) are isolated by contacting the strands with the streptavidin beads. Any combination of tagged primer and tag binding reagent may be utilized. Other suitable examples include haptenylated primers and beads or other reagents comprising an antibody or other antigen binding protein that binds to the hapten. Suitable haptens include, but are not limited to, pyrazoles, particularly nitropyrazoles; nitrophenyl compounds; benzofurazans; triterpenes; ureas and thioureas, particularly phenyl ureas, and even more particularly phenyl thioureas; rotenone and rotenone derivatives, also referred to herein as rotenoids; oxazole and thiazoles, particularly oxazole and thiazole sulfonamides; coumarin and coumarin derivatives; cyclolignans, exemplified by Podophyllotoxin and Podophyllotoxin derivatives; and combinations thereof. Specific examples of haptens include, but are not limited to, 2,4-Dintropheyl (DNP), Biotin, Fluorescein derivatives (FITC, TAMRA, Texas Red, etc.), Digoxygenin (DIG), 5-Nitro-3-pyrozolecarbamide (nitropyrazole, NP), 4,5,-Dimethoxy-2-nitrocinnamide (nitrocinnamide, NCA), 2-(3,4-Dimethoxyphenyl)-quinoline-4-carbamide (phenylquinolone, DPQ), 2,1,3-Benzoxadiazole-5-carbamide (benzofurazan, BF), 3-Hydroxy-2-quinoxalinecarbamide (hydroxyquinoxaline, HQ), 4-(Dimethylamino)azobenzene-4'-sulfonamide (DABSYL), Rotenone isoxazoline (Rot), (E)-2-(2-(2-oxo-2,3-dihydro-1H-benzo[b][1,4]diazepin-4-yl)phenozy)acetamide (benzodiazepine, BD), 7-(diethylamino)-2-oxo-2H-chromene-3-carboxylic acid (coumarin 343, CDO), 2-Acetamido-4-methyl-5-thiazolesulfonamide (thiazolesulfonamide, TS), and p-Mehtoxyphenylpyrazopodophyllamide (Podo).

In some embodiments, the 5hmC groups in the sample are modified with a blocking group to increase the ratio of methyl transferase efficiency between 5meC and 5hmC. As used herein, a "blocking group" is any chemical group that can be added to 5hmC (or cytosine at the 5-carbon position) that makes the total group too large, or unfavorably charged, for the DNA methyl transferase pocket, and thus blocks activity of a DNA methyl transferase at the 5hmC residue. It is contemplated that use of blocking groups increases the ratio of DNMT1 methyl transferase specificity and/or efficiency for catalyzing the transfer of a methyl group across from a 5meC and 5hmC in dsDNA. The present invention is not limited to the use of any particular blocking group. Suitable blocking groups include, but are not limited to Glucose (beta-glucose and alpha-glucose); Gentiobiose (6-O-β-D-glucopyranosyl-D-glucose) (and any other stereoisomer, the alpha linkage is also possible: 6-O-alpha-D-glucopyranosyl-D-glucose); keto-glucose; azide-glucose (e.g. N3 Glucose); a chemical group linked to the glucose or azide-glucose by, e.g., click chemistry, for example biotin (biotin-N3Glucose-5hmC); JBP1 (J-binding protein 1) bound to glu-5hmC (full length and truncated versions); TET proteins (e.g. TET1, TET2 and TET3) (full length and truncated versions) bind to 5hmC; other 5hmC or Glu-5hmC binding proteins and/or protein binding domains; (native and cross-linked versions of proteins); any oxidation product of glucose or modified glucose e.g. periodate oxidized glucose; any chemical group that can react with oxidized glucose to bind to or modify the glucose; and any protein or protein complex that can specifically identify either 5meC, 5hmC and modified variants of these bases (e.g., JBP1 and proteins of the MBP class (e.g., MBP1 and MeCP2)).

Without blocking, it is possibly to achieve 100% vs 0% vs 0% methyl transfer across from 5meC, C and 5hmC respectively, although the method is also applicable at less than 100% methyl transfer across from 5meC and more than 0% transfer across from C and 5hmC. Increased accuracy in quantification in such cases can be obtained when a known control is spiked into the sample so that the in-sample efficiency can be determined. With blocking it is possible to achieve 100% vs 0% vs 0% methyl transfer across from 5meC, C and 5hmC respectively, although the method is also applicable at less than 100% methyl transfer across from 5meC and more than 0% transfer across from C and 5hmC. Blocking may be useful for the "standard" assay as this will allow one to more robustly achieve 100% vs 0% vs 0% with the DNMT1 assay at a higher success rate as compared to without blocking.

With blocking, a 100% vs 100% vs 0% methyl transfer across from 5meC, C, 5hmC respectively for M.SssI (or DNMT1, preferably a large molar excess of DNMT1) is achievable. Methylation across from 5meC and C is an alternative way to transfer the information of the modification status from the parent strand to the replicated/primer extended strand to help in identifying 5meC, 5hmC and C positions and quantities. This can enable the direct read out of 5hmC as unmodified cytosines which are not protected from bisulfite conversion, or in comparison to standard bisulfite conversion and sequencing can reveal quantitative information for 5meC, C and 5hmC in the nucleic acid sequence. This will allow for the simple calculation to reveal the position and quantity of each of 5meC, C and 5hmC.

It is likely that 5meC, 5hmC and C identification can be achieved if blocking is performed at both 5hmC and C residues. Blocking agents at cytosine residues could for example be CXXC motif containing proteins or any protein or fragment thereof which can bind to unmodified CpG.

In some embodiments, the 5hmC diluted nucleic acid sample and an undiluted portion are treated to convert unmodified cytosine residues to thymidine residues. In preferred embodiments, the portions are treated with bisulfite to convert unmodified cytosine residues to uracil residues. The bisulfite-treated nucleic acid is then replicated with a polymerase to convert said uracil residues into thymidine residues. In some embodiments, the replication step is performed via one or more rounds of polymerase chain reaction (see, e.g., FIGS. 1 and 5) or primer extension reaction (See, e.g., FIG. 5). In preferred embodiments, a predetermined region is replicated by extension from nucleic acid primers defining the 5' and 3' boundaries of the predetermined region. In some embodiments, the number of cycles of replication may be greater than 2, 3, 5, 7, 10 or 20 cycles or between about 2 and 20 cycles.

The process described in the preceding paragraphs provides two different nucleic acid portions. In the first portion, the 5-hydroxymethylated residues have been diluted as compared to the 5-methylated cytosine residues, which have been maintained. In the second portion, the 5-hydroxymethylated residues have not been diluted. When the portions are treated with bisulfate, all non-modified cytosine residues are converted to uracil residues and then to thymidine residues following the 1 or more rounds of replication or primer extension. In preferred embodiments, both portions are sequenced, preferably utilizing primers that allow sequencing of the predetermined region. In preferred embodiments, comparison of the sequences of the first and second portions allow identification of 5meC and 5hmC residues in the predetermined region. 5hmC residues are identified as residues that are read by sequencing as a thymidine residue in the first portion (i.e., the portion in which 5hmC residues have been diluted) and as a cytosine residue at the corresponding position in the second nucleic acid portion and 5meC residues are identified as residues that are read as cytosine residues in both of the first and second nucleic acid portions.

Sequencing of the nucleic acid samples may be performed by any method known in the art. Suitable sequencing methods include, but are not limited to, chain termination sequencing methods (e.g., Sanger sequencing methods) and nextgen DNA sequencing methods utilizing systems provides by Illumina (San Diego Calif.), Pacific Biosciences (Menlo Park, Calif.) and others. In embodiments using nextgen sequencing methods, the step of replicating with a polymerase prior to sequencing (which converts the uracil residue to a thymidine residue) is optional and the uracil residue may be read directly.

In some embodiments, the processes described above are utilized for predicting a predisposition to a disease in a subject, diagnosing a disease in a subject, predicting the likelihood of recurrence of disease in a subject, providing a prognosis for a subject with a disease, or selecting a subject with a disease for treatment with a particular therapy. These process preferably comprise providing a genomic DNA sample from a subject; and detecting the methylation status of predetermined regions of the genomic DNA sample by the processes described above. In some embodiments, an altered level of 5-hydroxymethylcytosine and/or 5-methylcytosine methylation (i.e., a higher or lower level) of the predetermined regions of the genomic DNA to a reference methylation status provides an indication selected from the group consisting of an indication of a predisposition of the subject to a disease, an indication that the subject has a disease, an indication of the likelihood of recurrence of a disease in the subject, an indication of survival of the subject, and an indication that the subject is a candidate for treatment with a particular therapy.

Accordingly, in some embodiments, methods of the present invention involve the determination (e.g., assessment, ascertaining, quantitation) of 5meC and/or 5hmC modification level of an indicator of a condition of interest, such as a neoplasm in a sample. A skilled artisan understands that an increased, decreased, informative, or otherwise distinguishably different 5meC and/or 5hmC modification level is articulated with respect to a reference (e.g., a reference level, a control level, a threshold level, or the like). For example, the term "elevated 5hmC or 5meC level" as used herein with respect to the 5hmC or 5meC status of a gene locus is any 5hmC and/or 5meC level that is above a median 5hmC or 5meC level in a sample from a random population of mammals (e.g., a random population of 10, 20, 30, 40, 50, 100, or 500 mammals) that do not have a neoplasm (e.g., a cancer) or other condition of interest. Elevated levels of 5meC and/or 5hmC modification can be any level provided that the level is greater than a corresponding reference level. For example, an elevated 5meC and/or 5hmC level of a locus of interest can be 0.5, 1, 2, 3, 4, 5, 6, 7, 8, 9, 10, or more fold greater than the reference level 5meC and/or 5hmC observed in a normal sample. It is noted that a reference level can be any amount. The term "elevated 5meC and/or 5hmC score" as used herein with respect to detected 5meC and/or 5hmC events in a matrix panel of particular nucleic acid markers is any 5meC and/or 5hmC score that is above a median 5meC and/or 5hmC score in a sample from a random population of mammals (e.g., a random population of 10, 20, 30, 40, 50, 100, or 500 mammals) that do not have a neoplasm (e.g., a cancer). An elevated 5hmC score in a matrix panel of particular nucleic acid markers can be any score provided that the score is greater than a corresponding reference score. For example, an elevated score of 5meC and/or 5hmC in a locus of interest can be 0.5, 1, 2, 3, 4, 5, 6, 7, 8, 9, 10, or more fold greater than the reference 5meC and/or 5hmC score observed in a normal sample. It is noted that a reference score can be any amount that is used for comparison.

Similar considerations apply to assays for decreased levels of 5meC and/or 5hmC modifications in a sample, target locus, target genomic region and the like. For example, the term "decreased 5meC and/or 5hmC level" as used herein with respect to the 5meC and/or 5hmC status of a gene locus is any 5meC and/or 5hmC level that is below a median 5meC and/or 5hmC level in a sample from a random population of mammals (e.g., a random population of 10, 20, 30, 40, 50, 100, or 500 mammals) that do not have a neoplasm (e.g., a cancer). Decreased levels of 5meC and/or 5hmC modification can be any level provided that the level is less than a corresponding reference level. For example, a decreased 5meC and/or 5hmC level of a locus of interest can be 0.5, 1, 2, 3, 4, 5, 6, 7, 8, 9, 10, or more fold less than the reference level 5meC and/or 5hmC observed in a normal sample. It is noted that a reference level can be any amount. The term "decreased 5hmC score" as used herein with respect to detected 5meC and/or 5hmC events in a matrix panel of particular nucleic acid markers is any 5meC and/or 5hmC score that is below a median 5meC and/or 5hmC score in a sample from a random population of mammals (e.g., a random population of 10, 20, 30, 40, 50, 100, or 500 mammals) that do not have a neoplasm (e.g., a cancer). A decreased 5meC and/or 5hmC score in a matrix panel of particular nucleic acid markers can be any score provided that the score is greater than a corresponding reference score. For example, a decreased score of 5meC and/or 5hmC in a locus of interest can be 0.5, 1, 2, 3, 4, 5, 6, 7, 8, 9, 10, or more fold less than the reference 5meC and/or 5hmC score observed in a normal sample. It is noted that a reference score can be any amount that is used for comparison.

The methods are not limited to a particular type of mammal. In some embodiments, the mammal is a human. In some embodiments, the neoplasm is premalignant. In some embodiments, the neoplasm is malignant. In some embodiments, the neoplasm is cancer without regard to stage (e.g., stage I, II, III, or IV).

The present invention also provides methods and materials to assist medical or research professionals in determining whether or not a mammal has a neoplasm (e.g., cancer). Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the ratio of 5hmC and/or other markers in a sample, and (2) communicating information about the ratio to that professional, for example.

After the level (e.g., score or frequency) of particular 5meC and/or 5hmC modification in a sample is reported, a medical professional can take one or more actions that can affect patient care. For example, a medical professional can record the results in a patient's medical record. In some cases, a medical professional can record a diagnosis of a neoplasia, or otherwise transform the patient's medical record, to reflect the patient's medical condition. In some cases, a medical professional can review and evaluate a patient's entire medical record, and assess multiple treatment strategies, for clinical intervention of a patient's condition. In some cases, a medical professional can record a prediction of tumor occurrence with the reported indicators. In some cases, a medical professional can review and evaluate a patient's entire medical record and assess multiple treatment strategies, for clinical intervention of a patient's condition.

A medical professional can initiate or modify treatment of a neoplasm after receiving information regarding the level (score, frequency) associated with 5meC and/or 5hmC level in a patient's urine sample. In some cases, a medical professional can compare previous reports and the recently communicated level (score, frequency) of 5meC and/or 5hmC modification, and recommend a change in therapy. In some cases, a medical professional can enroll a patient in a clinical trial for novel therapeutic intervention of neoplasm. In some cases, a medical professional can elect waiting to begin therapy until the patient's symptoms require clinical intervention.

A medical professional can communicate the assay results to a patient or a patient's family. In some cases, a medical professional can provide a patient and/or a patient's family with information regarding neoplasia, including treatment options, prognosis, and referrals to specialists, e.g., oncologists and/or radiologists. In some cases, a medical professional can provide a copy of a patient's medical records to communicate assay results to a specialist. A research professional can apply information regarding a subject's assay results to advance neoplasm research. For example, a researcher can compile data on the assay results, with information regarding the efficacy of a drug for treatment of neoplasia to identify an effective treatment. In some cases, a research professional can obtain assay results to evaluate a subject's enrollment, or continued participation in a research study or clinical trial. In some cases, a research professional can classify the severity of a subject's condition, based on assay results. In some cases, a research professional can communicate a subject's assay results to a medical professional. In some cases, a research professional can refer a subject to a medical professional for clinical assessment of neoplasia, and treatment thereof. Any appropriate method can be used to communicate information to another person (e.g., a professional). For example, information can be given directly or indirectly to a professional. For example, a laboratory technician can input the assay results into a computer-based record. In some cases, information is communicated by making a physical alteration to medical or research records. For example, a medical professional can make a permanent notation or flag a medical record for communicating a diagnosis to other medical professionals reviewing the record. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

It is noted that a single sample can be analyzed for one neoplasm-specific marker or for multiple neoplasm-specific markers. In preferred embodiments, a single sample is analyzed for multiple neoplasm-specific markers, for example, using multi-marker assays. In addition, multiple samples can be collected for a single mammal and analyzed as described herein. In some embodiments, a sample is split into first and second portions, where the first portion undergoes cytological analysis and the second portion undergoes further purification or processing (e.g., sequence-specific capture step(s) (e.g., for isolation of specific loci for analysis of 5hmC levels). In some embodiments, the sample undergoes one or more preprocessing steps before being split into portions. In some embodiments, the sample is treated, handled, or preserved in a manner that promotes DNA integrity and/or inhibits DNA degradation (e.g., through use of storage buffers with stabilizing agents (e.g., chelating agents, DNase inhibitors) or handling or processing techniques that promote DNA integrity (e.g., immediate processing or storage at low temperature (e.g., −80 degrees C.)).

In some embodiments, all the basic essential materials and reagents required for detecting neoplasia through detecting both the level (presence, absence, score, frequency) of markers in a sample obtained from the mammal are assembled together in a kit. Such kits generally comprise, for example, reagents useful, sufficient, or necessary for detecting and/or characterizing one or more markers (e.g., epigenetic markers; 5hmC modifications) specific for a neoplasm. In some embodiments, the kits contain enzymes suitable for amplifying nucleic acids including various polymerases, deoxynucleotides and buffers to provide the necessary reaction mixture for amplification. In some embodiments, the kits of the present invention include a means for containing the reagents in close confinement for commercial sale such as, e.g., injection or blow-molded plastic containers into which the desired reagent are retained. Other containers suitable for conducting certain steps of the disclosed methods also may be provided.

In some embodiments, the methods disclosed herein are useful in monitoring the treatment of neoplasia (e.g., cancer). For example, in some embodiments, the methods may be performed immediately before, during and/or after a treatment to monitor treatment success. In some embodiments, the methods are performed at intervals on disease free patients to ensure treatment success.

The present invention also provides a variety of computer-related embodiments. Specifically, in some embodiments the invention provides computer programming for analyzing and comparing a pattern of neoplasm-specific marker detection results in a sample obtained from a subject to, for example, a library of such marker patterns known to be indicative of the presence or absence of a neoplasm, or a particular stage or neoplasm.

In some embodiments, the present invention provides computer programming for analyzing and comparing a first and a second pattern of neoplasm-specific marker detection results from a sample taken at least two different time points. In some embodiments, the first pattern may be indicative of a pre-cancerous condition and/or low risk condition for cancer and/or progression from a pre-cancerous condition to a cancerous condition. In such embodiments, the comparing provides for monitoring of the progression of the condition from the first time point to the second time point.

In yet another embodiment, the invention provides computer programming for analyzing and comparing a pattern of neoplasm-specific marker detection results from a sample to a library of neoplasm-specific marker patterns known to be indicative of the presence or absence of a cancer, wherein the comparing provides, for example, a differential diagnosis between a benign neoplasm, and an aggressively malignant neoplasm (e.g., the marker pattern provides for staging and/or grading of the cancerous condition).

The methods and systems described herein can be implemented in numerous ways. In one embodiment, the methods involve use of a communications infrastructure, for example the internet. Several embodiments of the invention are discussed below. It is also to be understood that the present invention may be implemented in various forms of hardware, software, firmware, processors, distributed servers (e.g., as used in cloud computing) or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of neoplasm-specific marker (e.g., epigenetic marker, 5hmC modification) detection results from a sample). This information received can be stored at least temporarily in a database, and data analyzed in comparison to a library of marker patterns known to be indicative of the presence or absence of a pre-cancerous condition, or known to be indicative of a stage and/or grade of cancer.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In some embodiments, all or a portion of the input data and/or all or a portion of the output data (e.g., usually at least the library of the pattern of neoplasm-specific marker detection results known to be indicative of the presence or absence of a pre-cancerous condition) are maintained on a server for access, e.g., confidential access. The results may be accessed or sent to professionals as desired.

A system for use in the methods described herein generally includes at least one computer processor (e.g., where the method is carried out in its entirety at a single site) or at least two networked computer processors (e.g., where detected marker data for a sample obtained from a subject is to be input by a user (e.g., a technician or someone performing the assays)) and transmitted to a remote site to a second computer processor for analysis (e.g., where the pattern of neoplasm-specific marker) detection results is compared to a library of patterns known to be indicative of the presence or absence of a pre-cancerous condition), where the first and second computer processors are connected by a network, e.g., via an intranet or internet). The system can also include a user component(s) for input; and a reviewer component(s) for review of data, and generation of reports, including detection of a pre-cancerous condition, staging and/or grading of a neoplasm, or monitoring the progression of a pre-cancerous condition or a neoplasm. Additional components of the system can include a server component(s); and a database(s) for storing data (e.g., as in a database of report elements, e.g., a library of marker patterns known to be indicative of the presence or absence of a pre-cancerous condition and/or known to be indicative of a grade and/or a stage of a neoplasm, or a relational database (RDB) which can include data input by the user and data output. The computer processors can be processors that are typically found in personal desktop computers (e.g., IBM, Dell, Macintosh), portable computers, mainframes, minicomputers, or other computing devices.

The input components can be complete, stand-alone personal computers offering a full range of power and features to run applications. The user component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe, or distributed across multiple servers (e.g., as in cloud computing applications) and offers data management, information sharing between clients, network administration and security. The application and any databases used can be on the same or different servers. Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

The present invention is useful for both the diagnosing diseases and disorders in a subject as well as determining the prognosis of a subject. The methods, reagents and systems of the present invention are applicable to a broad variety of diseases and disorders. In certain embodiments, the present invention provides methods for obtaining a subject's risk profile for developing neoplasm (e.g., cancer). In some embodiments, such methods involve obtaining a sample from a subject (e.g., a human at risk for developing cancer; a human undergoing a routine physical examination), detecting the presence, absence, or level (e.g., 5hmC modification frequency or score) of one or more markers specific for a neoplasm in or associated with the sample (e.g., specific for a neoplasm) in the sample, and generating a risk profile for developing neoplasm (e.g., cancer) based upon the detected level (score, frequency) or presence or absence of the indicators of neoplasia. For example, in some embodiments, a generated risk profile will change depending upon specific markers and detected as present or absent or at defined threshold levels. The present invention is not limited to a particular manner of generating the risk profile. In some embodiments, a processor (e.g., computer) is used to generate such a risk profile. In some embodiments, the processor uses an algorithm (e.g., software) specific for interpreting the presence and absence of specific 5hmC modifications as determined with the methods of the present invention. In some embodiments, the presence and absence of specific markers as determined with the methods of the present invention are inputed into such an algorithm, and the risk profile is reported based upon a comparison of such input with established norms (e.g., established norm for pre-cancerous condition, established norm for various risk levels for developing cancer, established norm for subjects diagnosed with various stages of cancer). In some embodiments, the risk profile indicates a subject's risk for developing cancer or a subject's risk for re-developing cancer. In some embodiments, the risk profile indicates a subject to be, for example, a very low, a low, a moderate, a high, and a very high chance of developing or re-developing cancer. In some embodiments, a health care provider (e.g., an oncologist) will use such a risk profile in determining a course of treatment or intervention (e.g., biopsy, wait and see, referral to an oncologist, referral to a surgeon, etc.).

Other diseases and disorders that may be diagnosed or prognosed with the methods, reagents and systems of the present invention include, but are not limited to, Prader-Willi syndrome, Angelman syndrome, Beckwith-Wiedemann syndrome, Pseudohypoparathyroidism, Russell-Silver syndrome, ICF syndrome, Rett syndrome, α-thalassemia/mental retardation, X-linked (ATR-X), Immunoosseous dysplasia, Schimke type, Rubinstein-Taybi syndrome, MTHFR deficiency, Recurrent hydatidiform mole, Fragile X mental retardation syndrome, Deletion LCR γδβ- and δβ-thalassemia, FSH dystrophy, disorders of XIC, Schimke immunoosseous dysplasia (SIOD), Sotos syndrome, Atrichia, X-linked Emery-Dreifuss muscular dystrophy (EDMD), Autosomal EDMD, CMT2B1, mandibuloacral dysplasia, limb-girdle muscular dystrophy type 1B, familial partial lipodystrophy, dilated cardiomyopathy 1A, Hutchinson-Gilford progeria syndrome, and Pelger-Huet anomaly.

The following examples are provided in order to demonstrate and further illustrate certain preferred embodiments and aspects of the present invention and are not to be construed as limiting the scope thereof.

Example 1

Figure 3A:
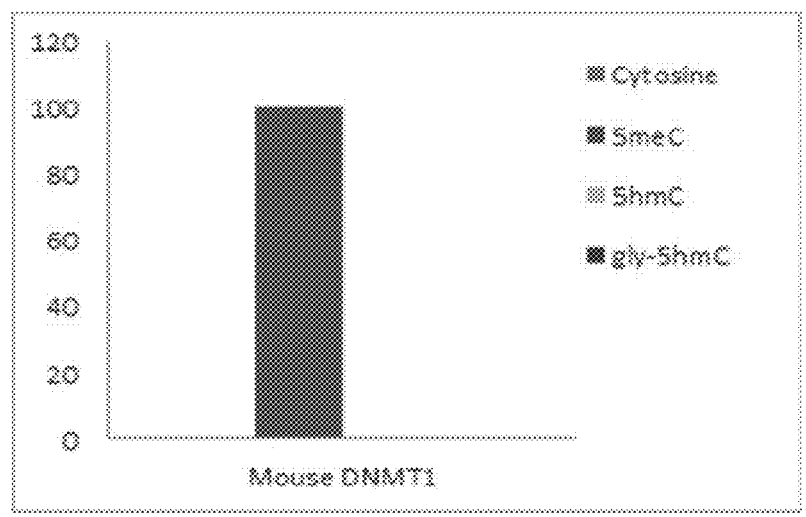
FIG. 3A-C. Mouse DNMT1, human DNMT1 and M.SssI preferentially methylate hemi-5meC DNA. 100 ng of each DNA substrate was incubated with 2 units mouse DNMT1, human DNMT1, or SssI methyltransferase as described in "materials and methods" section.
Figure 3B:
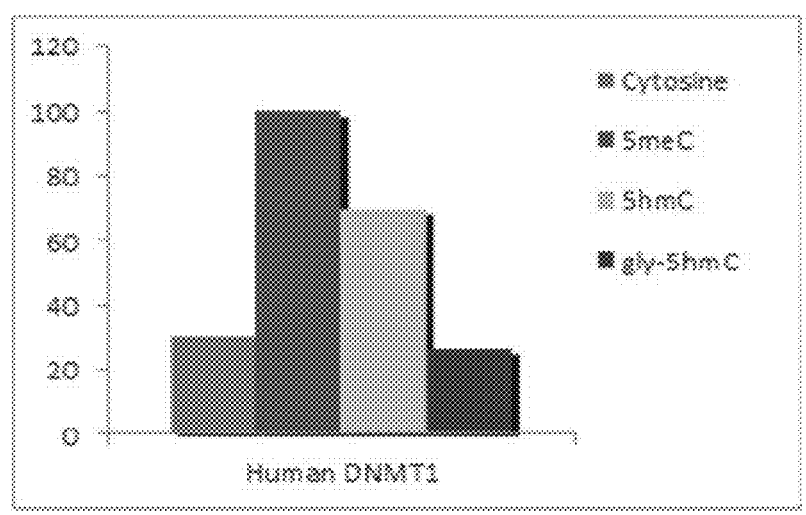
Figure 3C:
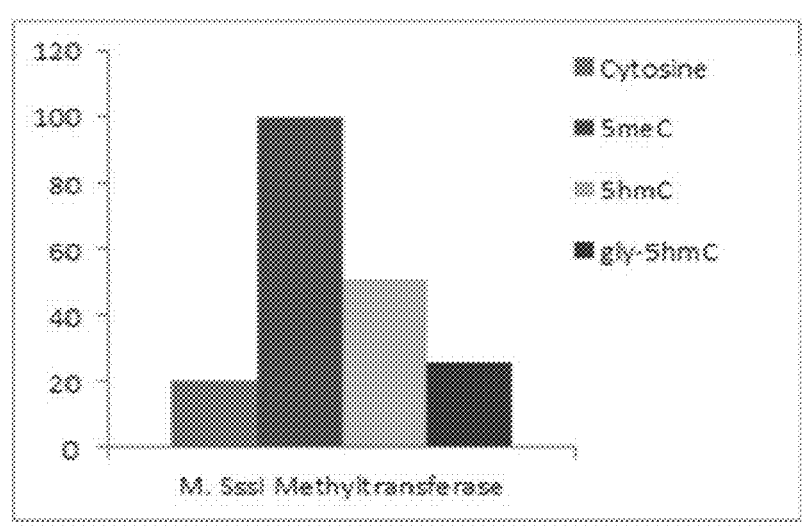
Figure 4A:
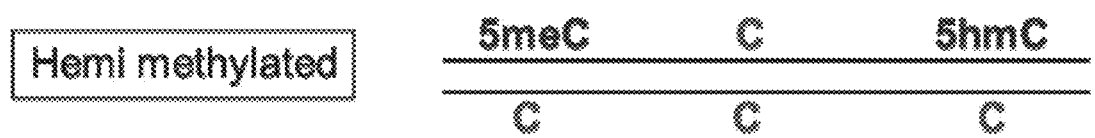
FIG. 4A-C. Validation of the feasibility of the 5hmC dilution assay. (A) The double stranded DNA oligo used in the validation contains three CpG sites where one is hemi for 5meC, a second one is having no modification and a third one is hemi for 5hmC. (B) Bisulfite conversion and sequencing of the unmodified bottom strand of the oligo in (A), when the oligo has not been subject to DNMT1 treatment, showed that all Cs were converted and read as T. (100% T is equal to 16 out of 16 individual clones being read as T at the C position of the CpG site). (C) Treatment with DNMT1 prior to bisulfite conversion and sequencing resulted in the addition of a methyl group to the unmethylated C of the CpG site hemi for 5meC in 87.5% of the oligoes. (Sequencing read a C at the C position of the CpG site in 14 out of 16 clones). No addition of a methyl group was observed across from C or 5hmC.
Figure 4B:
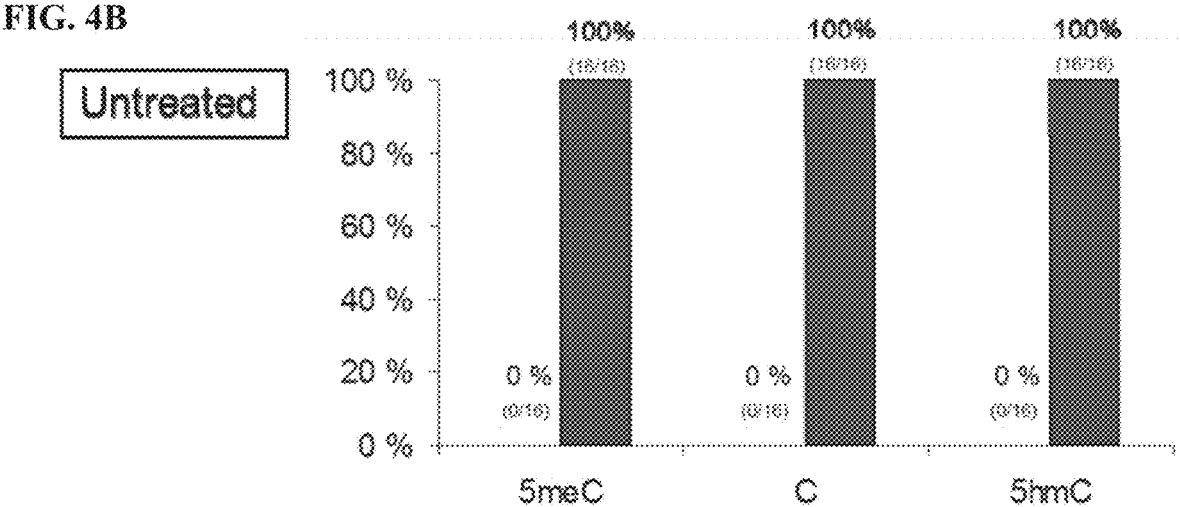
Figure 4C:
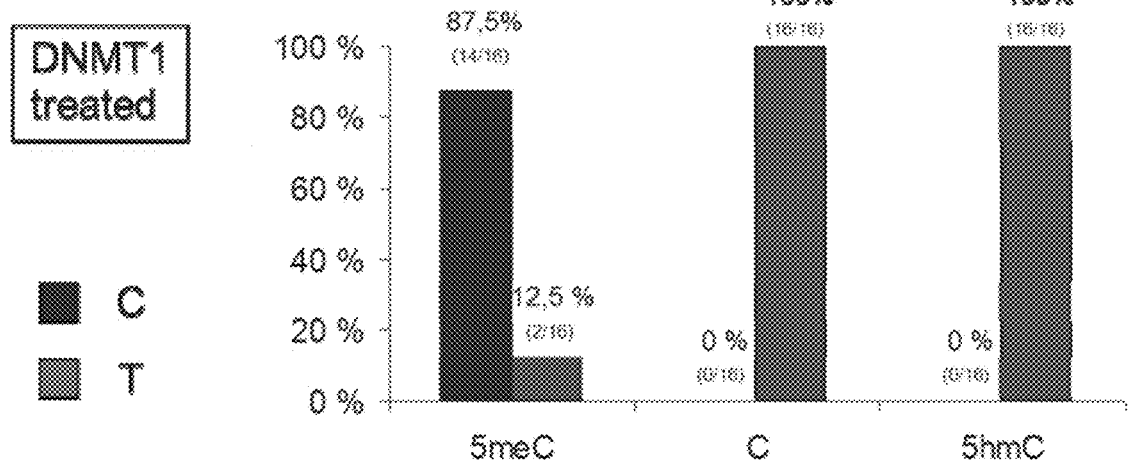

The method described here relies on the successive dilution by PCR of the 5hmC modification along with maintenance of the 5meC modification given that DNMT1 cannot methylate across from 5hmC and cytosine; however, DNMT1 can methylated DNA across from 5meC. FIGS. 3 and 4 demonstrate that DNMT1 cannot catalyze the transfer of a methyl group from S-adenosyl-methylmethionine when the DNA substrate is either a cytosine, 5hmC or a β-glucosyl-5hmC. Therefore, it is possible to dilute the 5hmC modification by PCR followed by treatment with DNMT1 while the 5meC modification will be maintained through multiple rounds of PCR and DNMT1 treatment.

Our method applies bisulfite conversion and sequencing of sample "A", untreated DNA, which will be used as a reference as it will detect the total of both 5meC and 5hmC. The method involves a 5hmC dilution assay, diluting 5hmC in the total pool of DNA fragments while maintaining 5meC. This dilution is achieved through sequential rounds of one cycle of PCR amplification (dilution) and treatment of the DNA with the DNA maintenance methyltransferase DNMT1 which enzymatically and specifically maintains 5meC by adding a methyl group uniquely to the unmethylated strand of the hemimethylated PCR products (this sample is referred to as sample "B" in FIG. 1). After a few rounds of this assay we apply bisulfite conversion and sequencing of the treated DNA sample, sample B, where 5meC now is the only modification present (or the only modification highly maintained). Therefore, all (or most) bases that read as C from this sample must have been protected against conversion because of 5meC and not 5hmC. By comparing "B" to the reference sample "A" we can easily detect all base positions containing 5hmC.

It should be noted that this method while effectively diluting 5hmC, it maintains the 5meC signal. Therefore, this method can serve two purposes (i) the identification of 5hmC in DNA and (ii) the identification of 5meC in DNA. The proof of feasibility of the assay described above is demonstrated in FIG. 4.

Experimental Design

The method described here relies on the successive dilution by PCR of the 5hmC modification along with maintenance of the 5meC modification given that DNMT1 cannot methylate across from 5hmC and cytosine; however, DNMT1 can methylate DNA across from 5meC. FIGS. 3A and 4 demonstrate that DNMT1 cannot catalyze the transfer of a methyl group from S-adenosyl-methylmethionine when the DNA substrate is either a cytosine, 5hmC or a b-glucosyl-5hmC. Therefore, it is possible to dilute the 5hmC modification by PCR followed by treatment with DNMT1 while the 5meC modification will be maintained through multiple rounds of PCR and DNMT1 treatment. Importantly, DNMT1 enzymes as well as other methyltransferases could be employed to distinguish between 5meC and 5hmC even when these enzymes do methylate across from 5hmC and cytosine as long the enzymes have a preference for the hemi 5meC over 5hmC, b-glucosyl-5hmC or cytosine at CpG sites (FIGS. 3B and C). Moreover, a DNMT1 or methyltransferase enzyme can allow for the identification of both 5meC and 5hmC in the assay described here even if the transfer of a methyl group from S-adenosyl-methylmethionine is of a much lower rate than 100%. The requirement for distinguishing 5meC from 5hmC is that there is a preference for 5meC over 5hmC, b-glucosyl-5hmC or cytosine at CpG sites (FIGS. 3B and C).

Our method applies bisulfite conversion and sequencing of sample "A", untreated DNA (FIG. 1), which will be used as a reference as it will detect the total of both 5meC and 5hmC. The method involves a 5hmC dilution assay, diluting 5hmC in the total pool of DNA fragments while maintaining 5meC. This dilution is achieved through sequential rounds of one cycle of PCR amplification (dilution) and treatment of the DNA with the DNA maintenance methyltransferase DNMT1 which enzymatically and specifically maintains 5meC by adding a methyl group uniquely to the unmethylated strand of the hemimethylated PCR products (this sample is referred to as sample "B" in FIG. 1). After a few rounds of this assay we apply bisulfite conversion and sequencing of the treated DNA sample, sample B, where 5meC now is the only modification present (or the only modification highly maintained). Therefore, all (or most) bases that read as C from this sample must have been protected against conversion because of 5meC and not 5hmC. By comparing "B" to the reference sample "A" we can easily detect all base positions containing 5hmC.

It should be noted that this method while effectively diluting 5hmC, it maintains the 5meC signal. Therefore, this method can serve two purposes (i) the identification of 5hmC in DNA and (ii) the identification of 5meC in DNA. The proof of feasibility of the assay described above is demonstrated in FIG. 4.

Furthermore, it should be noted that the current state of the art bisulfite conversion kits has limitations in the sensitivity. For example, the MethylEasy Xceed kit (Human Genetic Signatures, cat. no. ME002) allows for the analysis of 5meC from as few as 8 cells, but does not allow for single cell analysis. The method described here will while effectively diluting 5hmC and maintaining the 5meC signal allow for increased sensitivity of detection of both 5meC and 5hmC, with an obvious potential for single cell analysis as a result of the PCR amplification of the DNA sample (with either gene specific or whole genome amplification).

MATERIALS AND METHODS

Substrates

DNA substrates created by annealing the appropriate complementary oligonucleotide (see Supplemental Table 1) by heating to 95° C. and cooling at 1° C./min until the reaction reached 25° C. The methyltransferase specificity assay utilized oligonucleotides created by annealing either 5hmC top, 5meC top or cytosine top with cytosine bottom. The substrate used to simulate one round of PCR followed by DNMT1 treatment was created by annealing 5hmC:C:

5meC top with unmodified bottom. The substrate used for the full assay was created by annealing 5hmC:C:5meC top with 5hmC:C:5meC bottom.

Methyltransferase Specificity Assay

Reactions (50 µl) containing 100 ng DNA substrate (either cytosine, hemi-5meC, or hemi-5hmC), 50 mM Tris-HCl, 1 mM Dithiothreitol, 1 mM EDTA pH 8.0, 5% (v/v) Glycerol, S-[methyl-$^{14}$C]-Adenosyl-L-Methionine were incubated at 37° C. with 2 units of recombinant mouse DNMT1, recombinant human DNMT1, or SssI Methyltransferase for 30 minutes. Reactions were terminated by the addition of 200 µl TE buffer. The DNA from the reactions was ethanol precipitated and washed three times with ice-cold 70% ethanol. The DNA pellets were dried and suspended in 20 µl TE buffer. The entire reaction was transferred into a 5 ml Scintillation vial containing 2 ml Ecosinct A. The acid insoluble fractions were scintillation counted using an open window for 10 minutes.

Bisulfite Conversion, Cloning and Sequencing

Bisulfite conversion was carried out according to the user guide of the MethylEasy Xceed kit (Human Genetic Signatures, cat. no. ME002). Cloning was performed using the TOPO TA kit (Invitrogen, cat. no. K4595-40). Sequencing was carried out using the method described by Sanger.

Proof of Principle for the 5hmC Dilution Assay

A 112 bp dsDNA oligo containing three CpG sites where one is hemi-5meC, the second CpG contained no modification and the third CpG was hemi-5hmC, was used for a proof of principle of the 5hmC dilution assay. The oligo (65 ng) was added to a mixture of 5.0 µl 10× DNMT1-buffer (NEB), 2.5 µl of 3.2 mM SAM, 0.5 µl BSA (NEB, cat. no. B9001S) and 10 Units of mouse DNMT1 in a total volume of 50 µl adjusted with MqH$_2$O. The DNMT1 reactions were incubated on a Thermomixer at 37° C., 600 rpm for 4 h. The DNA oligoes were subsequently purified with a MinElute Reaction Cleanup Kit. Bisulfite conversion and sequencing of the unmodified bottom strand of the oligo was carried out before and after DNMT1 treatment.

The 5hmC Dilution Assay

A 112 bp dsDNA oligo containing three CpG sites, one having 5meC at both strands, a second one having no modification and a third one having 5hmC at both strands, was used to demonstrate the 5hmC dilution assay. To make hemi-modified oligonucleotides, PCR was set up and ran as following: The oligonucleotide (65 ng) was added to a mixture of 4.0 µl of 5× Phusion HF-buffer, 1.6 µl of 2.5 mM dNTPs, 1 µl of each of 10 µM forward and reverse primers, 0.2 µl of Phusion polymerase in a total volume of 20 µl adjusted with MqH$_2$O. Melting of the DNA strands was carried out for 3 min at 98° C., followed by primer annealing for 2 min at 56° C. and elongation for 8 min at 72° C. Next, the DNA was purified with a MinElute Reaction Cleanup Kit, the concentration was measured fluorimetrically on a Qubit instrument and DNMT1 treatment was carried out according to the following set up: The total amount of recovered oligo was added to a mixture of 5.0 µl 10× DNMT1-buffer (NEB), 2.5 µl of 3.2 mM SAM, 0.5 µl BSA (NEB, cat. no. B9001S) and 10 Units of mouse DNMT1 in a total volume of 50 µl adjusted with MqH$_2$O. The DNMT1 reactions were incubated on a Thermomixer at 37° C., 600 rpm for 4 h. Subsequently, 1 µl of Proteinase K was added (14-22 mg/ml) (Roche) and further incubation was carried out at 50° C. on a Thermomixer, 600 rpm for 1 h. The DNA oligoes was then ethanol precipitated and further purified with a MinElute Reaction Cleanup Kit. The DNA concentration was again measured fluorimetrically on a Qubit instrument. The setup described in this section can be carried out one or more times to result in a range of 5hmC dilution and 5meC conservation.

The 5hmC Dilution/Loss Assay Allowing for Strand Specific Assessment

A 112 bp dsDNA oligo containing three CpG sites, one having 5meC at both strands, a second one having no modification and a third one having 5hmC at both strands, was used to demonstrate the 5hmC dilution assay (also referred to as 5hmC loss assay and (biotin-)primer extension assay) making use of strand specific assessment. To make hemi-modified oligonucleotides, strand specific primer extension PCR was set up and ran as following: The oligonucleotide (65 ng) was added to a mixture of 4.0 µl of 5× Phusion HF-buffer, 1.6 µl of 2.5 mM dNTPs, 1 µl of only one of 10 µM forward and reverse primers containing a 5' biotin molecule/tag, 0.2 µl of Phusion polymerase in a total volume of 20 µl adjusted with MqH$_2$O. Melting of the DNA strands was carried out for 3 min at 98° C., followed by primer annealing for 2 min at 56° C. and elongation for 8 min at 72° C. Next, the DNA was purified with a Streptavidine coated magnetic beads and DNMT1 treatment was carried out according to the following set up: The total amount of recovered oligo was added to a mixture of 5.0 µl 10× DNMT1-buffer (NEB), 2.5 µl of 3.2 mM SAM, 0.5 µl BSA (NEB, cat. no. B9001S) and 10 Units of mouse DNMT1 in a total volume of 50 µl adjusted with MqH$_2$O. The DNMT1 reactions were incubated on a Thermomixer at 37° C., 600 rpm for 4 h. The boitinylated oligonucleotides were subsequently purified by using streptavidine magnetic beads and bisulfate converted, used as templates in PCR and sequenced.

Results

An outline the method is demonstrated in FIG. 1. To demonstrate the feasibility and success of the method we will demonstrate that (i) specific methyltransferases preferentially modify hemi-5meC DNA substrates, (ii) that this preference can be identified by bisulfite sequencing after treatment with the appropriate methyltransferase and (iii) the 5hmC modification can be diluted by successive rounds of DNA amplification followed by treatment with the appropriate DNA methylase.

Mouse DNMT1, Human DNMT1, and the M. SssI Methyltransferase Preferentially Methylate Hemi-5meC Substrates DNMT1 from mouse, DNMT1 from human and M. SssI methyltransferase were incubated with 100 ng of either unmodified, hemi-5meC, hemi-5hmC or hemi-beta-glucosyl-5hmC. Mouse DNMT1 was able to catalyze the transfer of a methyl group exclusively to the hemi-5meC substrate, showing no activity on the other substrates (FIG. 3A). Human DNMT1 shows an enzymatic preference for hemi-5meC while showing limited activity on the other substrates (FIG. 3B). Finally, the M. SssI methylase (*Spiroplasma* sp.)

also showed a preference for hemi-5meC containing DNA; (FIG. 3C). This result led us to the conclusion that any of these methyltransferases could suffice for the dilution assay described in FIG. 1.

Mouse DNMT1 Strongly Prefers Hemi-5meC as a Substrate

A dsDNA substrate containing a hemi-5meC, unmodified cytosine, and hemi-5hmC was incubated with mouse DNMT1 in the presence of S-adenosyl methylmethionine. DNA was cleaned and subjected to bisulfite sequencing as described in "Materials and Methods." After bisulfite sequencing we were able to demonstrate that nearly all (87.5%) of the hemi-5meC were fully methylated while the unmodified CpG and the hemi-5hmC were not modified by mouse DNMT1 (FIG. 4). As the substrate used for this assay mimics the fully 5hmC or fully-5hmC DNA after one round of amplification we determined that this assay would work if used with multiple rounds of DNA amplification and mouse DNMT1 treatment.

Successive Rounds of DNMT1 Treatment and PCR Amplification Can Dilute 5hmC While 5meC is Maintained A dsDNA substrate containing a fully-5meC, CpG, and fully-5hmC was amplified using Taq or Phusion polymerase followed by treatment with mouse DNMT1. This procedure was carried out three times as described in "materials and methods." FIG. 6B demonstrates the effective dilution of 5hmC while maintaining 5meC. It can be seen that prior to the dilution (FIG. 6A) the identity of 5hmC and 5meC cannot be distinguished; however, after the dilution treatment (FIG. 6B); 5hmC and 5meC can be clearly distinguished as the 5hmC is present at a greatly reduced amount compared to 5meC.

Strand Specific Primer Extension PCR Combined with the Use of Biotinylated Primers Allows for the Assessment of the Rate of DNMT1 Transfer of Methyl Groups to CpG Sites on a Newly Synthesized Strand at Sites Across from 5hmC, 5meC or C A dsDNA substrate containing a fully-5meC, CpG, and fully-5hmC was used as a template for strand specific primer extension PCR with primers containing a 5' biotin tag and followed by treatment with mouse DNMT1. The oligonucleotides that was newly synthesized was isolated to make sure that any methyation/signal at the three CpG sites of analysis of the strand chosen for study would not come from the parental copy of the same strand. The strategy allows for direct detection and quantification of the 5meC and 5hmC level without further rounds of the assay. Such an assay containing the oligonucleotide described in the materials and methods section can also be used as an internal reference and control to aid in the calculation of the content of modified C bases in genomic DNA samples.

Figure 12:
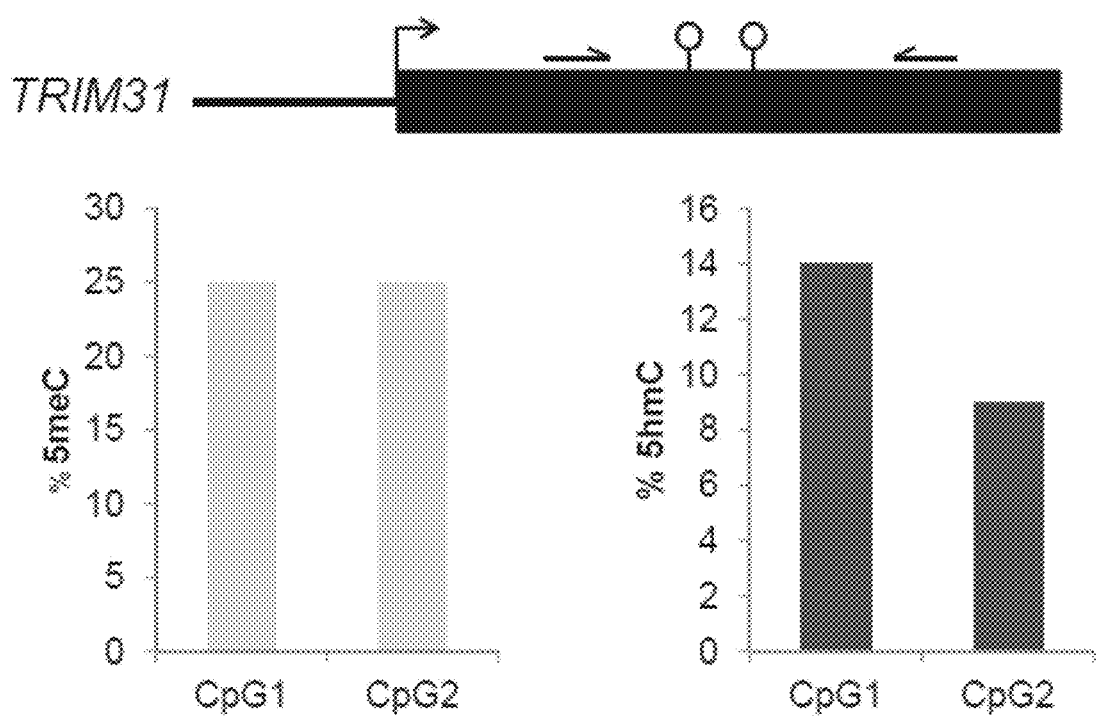
FIG. 12. Schematic and graphs showing identification of two 5hmC containing islands CpGs, that is 5hmC in a CG sequence, in the TRIM31 gene in human brain DNA using the assay depicted in FIG. 11. Positions of the CpGs are schematically depicted (not to scale) and the quantity of 5hmC and 5meC at those to cytosine positions are given in the bar graphs.

A representative protocol for the methyl transferase dependent assay (assay "B" in FIG. 11) is as follows:
Biotin-primer extension: "One round" PCR w/biotinylated primer
Pool PCR-products (from control oligo and genomic sample)
MinElute PCR Purification
Biotin-streptavidin purification with MyOne™ Streptavidin T1 beads
DNMT1 treatment on beads, 0.6-1 µl of 0.5 mg/ml DNMT1, 1.6 mM SAM, 37° C. in 30 min.
Washes; and elution in 50 µl MQ-H$_2$O 95° C. in 10 min.
MinElute Reaction Cleanup (optional)
Bisulfite treatment
Bisulfite PCR
TOPO TA cloning, transformation, selection on LB amp X-gal plates
Sequencing As shown in FIG. 12, the methyltransferase/DNMT1 dependent HyLo assay identified two 5hmC CpGs in the TRIM31 gene in human brain DNA. The assay outlined in FIG. 11 was used with genomic DNA spiked in with a control oligo containing known CpG sites for each of 5meC, C and 5hmC. Thus we could ensure accurate quantification of genomic DNA as we with the use of the oligo monitored the in-sample methyl transferase efficiency.

Example 2

Figure 13:
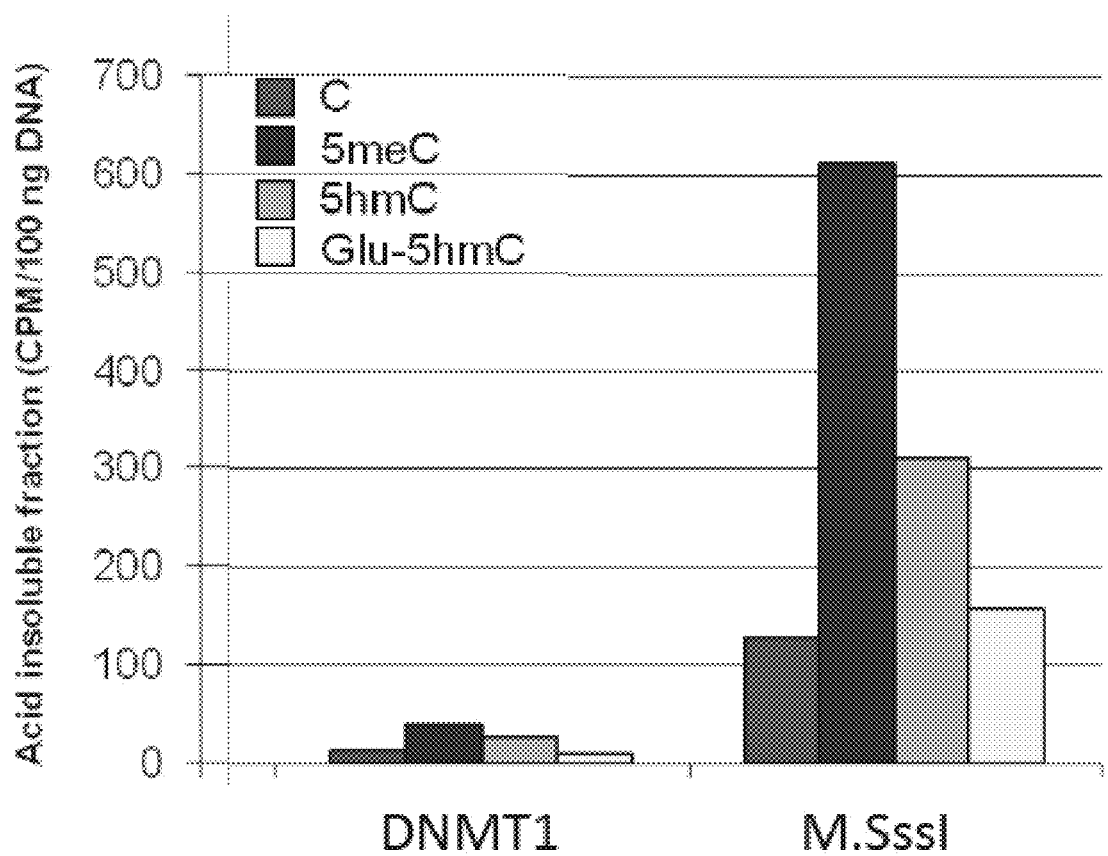
FIG. 13. Bar graph showing the results of an experiments where methyl transferase is blocked by addition of a chemical group to 5hmC.

Addition of a chemical group to 5hmC, such as glucose can be performed to increase the ratio of methyl transferase efficiency between 5meC and 5hmC. See FIG. 13. Sterical blocking of the methyl transferase at the modified 5hmC position can be taken advantage of to increase the robustness of the methyl transferase dependent assay. Here we show the blocking effect of the addition of a glucose to 5hmC in a radioactive methyl transferase assay. Both DNMT1 and M.SssI can be efficiently blocked by the addition of a chemical group with a size larger than what can fit into the methyl transferase pocket, for example by the addition of glucose. By logical reasoning from our data and the previous demonstration of that a cytosine carbon-5 group of —CCCH3 (size of 6.1 Å) does not fit into the methyl transferase pocket (Valinkluck and Sovers, Cancer Res, 2007) one can assume that the addition of any chemical group to 5hmC which makes the total group too large for the methyl transferase pocket will be useful to increase the ratio of methyl transferase efficiency between 5meC and 5hmC.

REFERENCES

1. Penn, N. W. Modification of brain deoxyribonucleic acid base content with maturation in normal and malnourished rats. *Biochem J* 155, 709-712 (1976).
2. Cannon-Carlson, S. V., Gokhale, H. & Teebor, G. W. Purification and characterization of 5-hydroxymethyluracil-DNA glycosylase from calf thymus. Its possible role in the maintenance of methylated cytosine residues. *J Biol Chem* 264, 13306-13312 (1989).
3. Tahiliani, M. et al. Conversion of 5-methylcytosine to 5-hydroxymethylcytosine in mammalian DNA by MLL partner TET1. *Science (New York, N.Y.* 324, 930-935 (2009).
4. Kriaucionis, S. & Heintz, N. The nuclear DNA base 5-hydroxymethylcytosine is present in Purkinje neurons and the brain. *Science (New York, N.Y.* 324, 929-930 (2009).
5. Ito, S. et al. Role of Tet proteins in 5mC to 5hmC conversion, ES-cell self-renewal and inner cell mass specification. *Nature* 466, 1129-1133 (2010).
6. Szwagierczak, A., Bultmann, S., Schmidt, C. S., Spada, F. & Leonhardt, H. Sensitive enzymatic quantification of 5-hydroxymethylcytosine in genomic DNA. *Nucleic acids research* 38, e181 (2010).

7. Ko, M. et al. Impaired hydroxylation of 5-methylcytosine in myeloid cancers with mutant TET2. *Nature* 468, 839-843 (2010).
8. Guo, J. U., Su, Y., Zhong, C., Ming, G. L. & Song, H. Hydroxylation of 5-methylcytosine by TET1 promotes active DNA demethylation in the adult brain. *Cell* 145, 423-434 (2011).
9. Wu, H. et al. Genome-wide analysis of 5-hydroxymethylcytosine distribution reveals its dual function in transcriptional regulation in mouse embryonic stem cells. *Genes & development* 25, 679-684 (2011).
10. Wu, H. et al. Dual functions of Tet1 in transcriptional regulation in mouse embryonic stem cells. *Nature* (2011).
11. Robertson, J., Robertson, A. B. & Klungland, A. The Presence of 5-hydroxymethylcytosine at the gene promoter and not in the gene body negatively regulates gene expression. *Biochem Biophys Res Comm* (2011).
12. Robertson, A. B. et al. A novel method for the efficient and selective identification of 5-hydroxymethylcytosine in genomic DNA. *Nucleic acids research* 39, e55 (2011).
13. Georgopoulos, C. P. & Revel, H. R. Studies with glucosyl transferase mutants of the T-even bacteriophages. *Virology* 44, 271-285 (1971).
14. Kornberg, S. R., Zimmerman, S. B. & Kornberg, A. Glucosylation of deoxyribonucleic acid by enzymes from bacteriophage-infected *Escherichia coli. J Biol Chem* 236, 1487-1493 (1961).
15. Gommers-Ampt, J. H. et al. beta-D-glucosyl-hydroxymethyluracil: a novel modified base present in the DNA of the parasitic protozoan *T. brucei. Cell* 75, 1129-1136 (1993).
16. Borst, P. & Sabatini, R. Base J: discovery, biosynthesis, and possible functions. *Annu Rev Microbiol* 62, 235-251 (2008).
17. van Leeuwen, F. et al. beta-D-glucosyl-hydroxymethyluracil is a conserved DNA modification in kinetoplastid protozoans and is abundant in their telomeres. *Proc Natl Acad Sci USA* 95, 2366-2371 (1998).
18. Sabatini, R., Meeuwenoord, N., van Boom, J. H. & Borst, P. Recognition of base J in duplex DNA by J-binding protein. *J Biol Chem* 277, 958-966 (2002).
19. Cross, M. et al. The modified base J is the target for a novel DNA-binding protein in kinetoplastid protozoans. *EMBO J* 18, 6573-6581 (1999).
20. Grover, R. K. et al. O-glycoside orientation is an essential aspect of base J recognition by the kinetoplastid DNA-binding protein JBP1. *Angewandte Chemie (International ed* 46, 2839-2843 (2007).
21. Ficz, G. et al. Dynamic regulation of 5-hydroxymethylcytosine in mouse ES cells and during differentiation. *Nature* (2011).
22. Stroud, H., Feng, S., Morey Kinney, S., Pradhan, S. & Jacobsen, S. E. 5-hydroxymethylcytosine is associated with enhancers and gene bodies in human embryonic stem cells. *Genome Biol* 12, R54 (2011).
23. Pastor, W. A. et al. Genome-wide mapping of 5-hydroxymethylcytosine in embryonic stem cells. *Nature* 473, 394-397 (2011).
24. Flusberg, B. A. et al. Direct detection of DNA methylation during single-molecule, real-time sequencing. *Nat Methods* 7, 461-465 (2010).
25. Song, C. X., Yu, M., Dai, Q. & He, C. Detection of 5-hydroxymethylcytosine in a combined glycosylation restriction analysis (CGRA) using restriction enzyme Taq(alpha)I. *Bioorg Med Chem Lett* (2011).
26. Xu, S. Y., Corvaglia, A. R., Chan, S. H., Zheng, Y. & Linder, P. A type IV modification-dependent restriction enzyme SauUSI from *Staphylococcus aureus* subsp. *aureus* USA300. *Nucleic acids research* (2011).
27. Szwagierczak, A. et al. Characterization of PvuRts1I endonuclease as a tool to investigate genomic 5-hydroxymethylcytosine. *Nucleic acids research* (2011).
28. Song, C. X. et al. Selective chemical labeling reveals the genome-wide distribution of 5-hydroxymethylcytosine. *Nature biotechnology* 29, 68-72 (2011).
29. Ficz, G. et al. Dynamic regulation of 5-hydroxymethylcytosine in mouse ES cells and during differentiation. *Nature* 473, 398-402 (2011).
30. Nestor, C., Ruzov, A., Meehan, R. & Dunican, D. Enzymatic approaches and bisulfite sequencing cannot distinguish between 5-methylcytosine and 5-hydroxymethylcytosine in DNA. *Biotechniques* 48, 317-319 (2010).
31. Studier, F. W. Protein production by auto-induction in high density shaking cultures. *Protein Expr Purif* 41, 207-234 (2005).
32. Zhang, Y. et al. Model-based analysis of ChIP-Seq (MACS). *Genome Biol* 9, R137 (2008).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical, biological and chemical sciences are intended to be within the scope of the following claims.

We claim:

1. A method for detecting 5-methylated cytosine and 5-hydroxymethylated cytosine of a nucleic acid sequence, wherein said method comprising:
   (a) contacting a nucleic acid methyltransferase with said nucleic acid sequence and a daughter sequence of said nucleic acid sequence, which daughter sequence comprises a complementary sequence of said nucleic acid sequence, such that a pattern of 5-methylated cytosine residues of said nucleic acid sequence is maintained;
   (b) after (a), oxidizing unmodified cytosine of said nucleic acid sequence and of said daughter sequence to yield a modified nucleic acid sequence and a modified daughter sequence;
   (c) sequencing said modified nucleic acid sequence or derivative thereof and said modified daughter sequence or derivative thereof to obtain a first sequence corresponding to said modified nucleic acid sequence and a second sequence corresponding to said modified daughter sequence; and
   (d) comparing said first sequence and said second sequence to identify and distinguish said 5-methylated cytosine and said 5-hydroxymethylated cytosine of said nucleic acid sequence.

2. The method of claim 1, wherein a hemimethylated double stranded nucleic acid sequence comprises said nucleic acid sequence and said daughter sequence.

3. The method of claim 1, wherein said nucleic acid sequence comprises genomic DNA.

4. The method of claim 1, wherein said nucleic acid methyltransferase is a DNA methyltransferase.

5. The method of claim 4, wherein said DNA methyltransferase is DNMT1.

6. The method of claim 5, wherein said DNMT1 comprises a sequence corresponding to SEQ ID NO: 1 or SEQ ID NO: 2.

7. The method of claim 4, wherein said DNA methyltransferase is M.SssI DNMT.

8. The method of claim 7, wherein said M.SssI DNMT comprises a sequence corresponding to SEQ ID NO: 3.

9. The method of claim 1, wherein said oxidizing comprises treating unmodified cytosine on said nucleic acid sequence and on said daughter sequence with bisulfite.

10. The method of claim 1, wherein said 5-hydroxymethylated cytosine comprises 5-hydroxymethyl cytosine or beta-glu-5-hydroxymethyl cytosine.

11. The method of claim 10, wherein said 5-hydroxymethylated cytosine comprises 5-hydroxymethyl cytosine.

12. The method of claim 1, wherein said sequencing comprises a next generation sequencing method.

13. The method of claim 1, wherein said nucleic acid sequence is obtained from a subject having or suspected of having a disease or condition.

14. The method of claim 13, wherein said disease or condition comprises cancer.

15. The method of claim 1, wherein said 5-methylated cytosine and 5-hydroxymethylated cytosine are identified at base specific resolution.

\* \* \* \* \*

SEQUENCE LISTING

```
<160> NUMBER OF SEQ ID NOS: 15

<210> SEQ ID NO 1
<211> LENGTH: 1627
<212> TYPE: PRT
<213> ORGANISM: Mus musculus

<400> SEQUENCE: 1

Met Pro Ala Arg Thr Ala Pro Ala Arg Val Pro Ala Leu Ala Ser Pro
1               5                   10                  15

Ala Gly Ser Leu Pro Asp His Val Arg Arg Arg Leu Lys Asp Leu Glu
```

```
                20                  25                  30
Arg Asp Gly Leu Thr Glu Lys Glu Cys Val Arg Glu Lys Leu Asn Leu
                35                  40                  45

Leu His Glu Phe Leu Gln Thr Glu Ile Lys Ser Gln Leu Cys Asp Leu
 50                  55                  60

Glu Thr Lys Leu His Lys Glu Glu Leu Ser Glu Gly Tyr Leu Ala
 65                  70                  75                  80

Lys Val Lys Ser Leu Leu Asn Lys Asp Leu Ser Leu Glu Asn Gly Thr
                85                  90                  95

His Thr Leu Thr Gln Lys Ala Asn Gly Cys Pro Ala Asn Gly Ser Arg
                100                 105                 110

Pro Thr Trp Arg Ala Glu Met Ala Asp Ser Asn Arg Ser Pro Arg Ser
                115                 120                 125

Arg Pro Lys Pro Arg Gly Pro Arg Arg Ser Lys Ser Asp Ser Asp Thr
                130                 135                 140

Leu Cys Lys Asp Thr Arg His Thr Ala Val Glu Thr Ser Pro Ser Ser
145                 150                 155                 160

Val Ala Thr Arg Arg Thr Thr Arg Gln Thr Thr Ile Thr Ala His Phe
                165                 170                 175

Thr Lys Gly Pro Thr Lys Arg Lys Pro Lys Glu Ser Glu Glu Gly
                180                 185                 190

Asn Ser Ala Glu Ser Ala Ala Glu Glu Arg Asp Gln Asp Lys Lys Arg
                195                 200                 205

Arg Val Val Asp Thr Glu Ser Gly Ala Ala Ala Val Glu Lys Leu
                210                 215                 220

Glu Glu Val Thr Ala Gly Thr Gln Leu Gly Pro Glu Pro Cys Glu
225                 230                 235                 240

Gln Glu Asp Asp Asn Arg Ser Leu Arg Arg His Thr Arg Glu Leu Ser
                245                 250                 255

Leu Arg Arg Lys Ser Lys Glu Asp Pro Asp Arg Glu Ala Arg Pro Glu
                260                 265                 270

Thr His Leu Asp Glu Asp Glu Asp Gly Lys Lys Asp Lys Arg Ser Ser
                275                 280                 285

Arg Pro Arg Ser Gln Pro Arg Asp Pro Ala Ala Lys Arg Arg Pro Lys
                290                 295                 300

Glu Ala Glu Pro Glu Gln Val Ala Pro Glu Thr Pro Glu Asp Arg Asp
305                 310                 315                 320

Glu Asp Glu Arg Glu Glu Lys Arg Arg Lys Thr Thr Arg Lys Lys Leu
                325                 330                 335

Glu Ser His Thr Val Pro Val Gln Ser Arg Ser Glu Arg Lys Ala Ala
                340                 345                 350

Gln Ser Lys Ser Val Ile Pro Lys Ile Asn Ser Pro Lys Cys Pro Glu
                355                 360                 365

Cys Gly Gln His Leu Asp Asp Pro Asn Leu Lys Tyr Gln Gln His Pro
                370                 375                 380

Glu Asp Ala Val Asp Glu Pro Gln Met Leu Thr Ser Glu Lys Leu Ser
385                 390                 395                 400

Ile Tyr Asp Ser Thr Ser Thr Trp Phe Asp Tyr Glu Asp Ser Pro
                405                 410                 415

Met His Arg Phe Thr Ser Phe Ser Val Tyr Cys Ser Arg Gly His Leu
                420                 425                 430

Cys Pro Val Asp Thr Gly Leu Ile Glu Lys Asn Val Glu Leu Tyr Phe
                435                 440                 445
```

```
Ser Gly Cys Ala Lys Ala Ile His Asp Glu Asn Pro Ser Met Glu Gly
    450                 455                 460

Gly Ile Asn Gly Lys Asn Leu Gly Pro Ile Asn Gln Trp Trp Leu Ser
465                 470                 475                 480

Gly Phe Asp Gly Gly Glu Lys Val Leu Ile Gly Phe Ser Thr Ala Phe
                485                 490                 495

Ala Glu Tyr Ile Leu Met Glu Pro Ser Lys Glu Tyr Glu Pro Ile Phe
            500                 505                 510

Gly Leu Met Gln Glu Lys Ile Tyr Ile Ser Lys Ile Val Glu Phe
        515                 520                 525

Leu Gln Asn Asn Pro Asp Ala Val Tyr Glu Asp Leu Ile Asn Lys Ile
    530                 535                 540

Glu Thr Thr Val Pro Pro Ser Thr Ile Asn Val Asn Arg Phe Thr Glu
545                 550                 555                 560

Asp Ser Leu Leu Arg His Ala Gln Phe Val Val Ser Gln Val Glu Ser
                565                 570                 575

Tyr Asp Glu Ala Lys Asp Asp Glu Thr Pro Ile Phe Leu Ser Pro
            580                 585                 590

Cys Met Arg Ala Leu Ile His Leu Ala Gly Val Ser Leu Gly Gln Arg
                595                 600                 605

Arg Ala Thr Arg Arg Val Met Gly Ala Thr Lys Glu Lys Asp Lys Ala
    610                 615                 620

Pro Thr Lys Ala Thr Thr Lys Leu Val Tyr Gln Ile Phe Asp Thr
625                 630                 635                 640

Phe Phe Ser Glu Gln Ile Glu Lys Tyr Asp Lys Glu Asp Lys Glu Asn
                645                 650                 655

Ala Met Lys Arg Arg Cys Gly Val Cys Glu Val Cys Gln Gln Pro
            660                 665                 670

Glu Cys Gly Lys Cys Lys Ala Cys Lys Asp Met Val Lys Phe Gly Gly
        675                 680                 685

Thr Gly Arg Ser Lys Gln Ala Cys Leu Lys Arg Arg Cys Pro Asn Leu
    690                 695                 700

Ala Val Lys Glu Ala Asp Asp Glu Glu Ala Asp Asp Val Ser
705                 710                 715                 720

Glu Met Pro Ser Pro Lys Lys Leu His Gln Gly Lys Lys Lys Gln
                725                 730                 735

Asn Lys Asp Arg Ile Ser Trp Leu Gly Gln Pro Met Lys Ile Glu Glu
            740                 745                 750

Asn Arg Thr Tyr Tyr Gln Lys Val Ser Ile Asp Glu Met Leu Glu
        755                 760                 765

Val Gly Asp Cys Val Ser Val Ile Pro Asp Asp Ser Ser Lys Pro Leu
    770                 775                 780

Tyr Leu Ala Arg Val Thr Ala Leu Trp Glu Asp Lys Asn Gly Gln Met
785                 790                 795                 800

Met Phe His Ala His Trp Phe Cys Ala Gly Thr Asp Thr Val Leu Gly
                805                 810                 815

Ala Thr Ser Asp Pro Leu Glu Leu Phe Leu Val Gly Glu Cys Glu Asn
            820                 825                 830

Met Gln Leu Ser Tyr Ile His Ser Lys Val Lys Val Ile Tyr Lys Ala
        835                 840                 845

Pro Ser Glu Asn Trp Ala Met Glu Gly Gly Thr Asp Pro Glu Thr Thr
    850                 855                 860
```

```
Leu Pro Gly Ala Glu Asp Gly Lys Thr Tyr Phe Gln Leu Trp Tyr
865                 870                 875                 880

Asn Gln Glu Tyr Ala Arg Phe Glu Ser Pro Pro Lys Thr Gln Pro Thr
                885                 890                 895

Glu Asp Asn Lys His Lys Phe Cys Leu Ser Cys Ile Arg Leu Ala Glu
                900                 905                 910

Leu Arg Gln Lys Glu Met Pro Lys Val Leu Glu Gln Ile Glu Glu Val
            915                 920                 925

Asp Gly Arg Val Tyr Cys Ser Ser Ile Thr Lys Asn Gly Val Val Tyr
        930                 935                 940

Arg Leu Gly Asp Ser Val Tyr Leu Pro Pro Glu Ala Phe Thr Phe Asn
945                 950                 955                 960

Ile Lys Val Ala Ser Pro Val Lys Arg Pro Lys Lys Asp Pro Val Asn
                965                 970                 975

Glu Thr Leu Tyr Pro Glu His Tyr Arg Lys Tyr Ser Asp Tyr Ile Lys
                980                 985                 990

Gly Ser Asn Leu Asp Ala Pro Glu Pro Tyr Arg Ile Gly Arg Ile Lys
                995                 1000                1005

Glu Ile His Cys Gly Lys Lys Lys Gly Lys Val Asn Glu Ala Asp
    1010                1015                1020

Ile Lys Leu Arg Leu Tyr Lys Phe Tyr Arg Pro Glu Asn Thr His
    1025                1030                1035

Arg Ser Tyr Asn Gly Ser Tyr His Thr Asp Ile Asn Met Leu Tyr
    1040                1045                1050

Trp Ser Asp Glu Glu Ala Val Val Asn Phe Ser Asp Val Gln Gly
    1055                1060                1065

Arg Cys Thr Val Glu Tyr Gly Glu Asp Leu Leu Glu Ser Ile Gln
    1070                1075                1080

Asp Tyr Ser Gln Gly Gly Pro Asp Arg Phe Tyr Phe Leu Glu Ala
    1085                1090                1095

Tyr Asn Ser Lys Thr Lys Asn Phe Glu Asp Pro Pro Asn His Ala
    1100                1105                1110

Arg Ser Pro Gly Asn Lys Gly Lys Gly Lys Gly Lys Gly Lys Gly
    1115                1120                1125

Lys Gly Lys His Gln Val Ser Glu Pro Lys Glu Pro Glu Ala Ala
    1130                1135                1140

Ile Lys Leu Pro Lys Leu Arg Thr Leu Asp Val Phe Ser Gly Cys
    1145                1150                1155

Gly Gly Leu Ser Glu Gly Phe His Gln Ala Gly Ile Ser Glu Thr
    1160                1165                1170

Leu Trp Ala Ile Glu Met Trp Asp Pro Ala Ala Gln Ala Phe Arg
    1175                1180                1185

Leu Asn Asn Pro Gly Thr Thr Val Phe Thr Glu Asp Cys Asn Val
    1190                1195                1200

Leu Leu Lys Leu Val Met Ala Gly Glu Val Thr Asn Ser Leu Gly
    1205                1210                1215

Gln Arg Leu Pro Gln Lys Gly Asp Val Glu Met Leu Cys Gly Gly
    1220                1225                1230

Pro Pro Cys Gln Gly Phe Ser Gly Met Asn Arg Phe Asn Ser Arg
    1235                1240                1245

Thr Tyr Ser Lys Phe Lys Asn Ser Leu Val Val Ser Phe Leu Ser
    1250                1255                1260

Tyr Cys Asp Tyr Tyr Arg Pro Arg Phe Phe Leu Leu Glu Asn Val
```

1265                  1270                  1275

Arg Asn Phe Val Ser Tyr Arg Arg Ser Met Val Leu Lys Leu Thr
            1280                  1285                  1290

Leu Arg Cys Leu Val Arg Met Gly Tyr Gln Cys Thr Phe Gly Val
        1295                  1300                  1305

Leu Gln Ala Gly Gln Tyr Gly Val Ala Gln Thr Arg Arg Arg Ala
    1310                  1315                  1320

Ile Ile Leu Ala Ala Ala Pro Gly Glu Lys Leu Pro Leu Phe Pro
1325                  1330                  1335

Glu Pro Leu His Val Phe Ala Pro Arg Ala Cys Gln Leu Ser Val
    1340                  1345                  1350

Val Val Asp Asp Lys Lys Phe Val Ser Asn Ile Thr Arg Leu Ser
1355                  1360                  1365

Ser Gly Pro Phe Arg Thr Ile Thr Val Arg Asp Thr Met Ser Asp
1370                  1375                  1380

Leu Pro Glu Ile Gln Asn Gly Ala Ser Asn Ser Glu Ile Pro Tyr
        1385                  1390                  1395

Asn Gly Glu Pro Leu Ser Trp Phe Gln Arg Gln Leu Arg Gly Ser
1400                  1405                  1410

His Tyr Gln Pro Ile Leu Arg Asp His Ile Cys Lys Asp Met Ser
    1415                  1420                  1425

Pro Leu Val Ala Ala Arg Met Arg His Ile Pro Leu Phe Pro Gly
1430                  1435                  1440

Ser Asp Trp Arg Asp Leu Pro Asn Ile Gln Val Arg Leu Gly Asp
    1445                  1450                  1455

Gly Val Ile Ala His Lys Leu Gln Tyr Thr Phe His Asp Val Lys
1460                  1465                  1470

Asn Gly Tyr Ser Ser Thr Gly Ala Leu Arg Gly Val Cys Ser Cys
    1475                  1480                  1485

Ala Glu Gly Lys Ala Cys Asp Pro Glu Ser Arg Gln Phe Ser Thr
1490                  1495                  1500

Leu Ile Pro Trp Cys Leu Pro His Thr Gly Asn Arg His Asn His
    1505                  1510                  1515

Trp Ala Gly Leu Tyr Gly Arg Leu Glu Trp Asp Gly Phe Phe Ser
1520                  1525                  1530

Thr Thr Val Thr Asn Pro Glu Pro Met Gly Lys Gln Gly Arg Val
1535                  1540                  1545

Leu His Pro Glu Gln His Arg Val Val Ser Val Arg Glu Cys Ala
1550                  1555                  1560

Arg Ser Gln Gly Phe Pro Asp Ser Tyr Arg Phe Phe Gly Asn Ile
1565                  1570                  1575

Leu Asp Arg His Arg Gln Val Gly Asn Ala Val Pro Pro Pro Leu
    1580                  1585                  1590

Ala Lys Ala Ile Gly Leu Glu Ile Lys Leu Cys Leu Leu Ser Ser
1595                  1600                  1605

Ala Arg Glu Ser Ala Ser Ala Ala Val Lys Ala Lys Glu Glu Ala
    1610                  1615                  1620

Ala Thr Lys Asp
1625

<210> SEQ ID NO 2
<211> LENGTH: 1632
<212> TYPE: PRT
<213> ORGANISM: Homo sapiens

<400> SEQUENCE: 2

```
Met Pro Ala Arg Thr Ala Pro Ala Arg Val Pro Thr Leu Ala Val Pro
1               5                   10                  15

Ala Ile Ser Leu Pro Asp Asp Val Arg Arg Leu Lys Asp Leu Glu
            20                  25                  30

Arg Asp Ser Leu Thr Glu Lys Glu Cys Val Lys Glu Lys Leu Asn Leu
            35                  40                  45

Leu His Glu Phe Leu Gln Thr Glu Ile Lys Asn Gln Leu Cys Asp Leu
        50                  55                  60

Glu Thr Lys Leu Arg Lys Glu Glu Leu Ser Glu Glu Gly Tyr Leu Ala
65              70                  75                  80

Lys Val Lys Ser Leu Leu Asn Lys Asp Leu Ser Leu Glu Asn Gly Ala
                85                  90                  95

His Ala Tyr Asn Arg Glu Val Asn Gly Arg Leu Glu Asn Gly Asn Gln
            100                 105                 110

Ala Arg Ser Glu Ala Arg Arg Val Gly Met Ala Asp Ala Asn Ser Pro
            115                 120                 125

Pro Lys Pro Leu Ser Lys Pro Arg Thr Pro Arg Arg Ser Lys Ser Asp
130                 135                 140

Gly Glu Ala Lys Arg Ser Arg Asp Pro Pro Ala Ser Ala Ser Gln Val
145                 150                 155                 160

Thr Gly Ile Arg Ala Glu Pro Ser Pro Ser Pro Arg Ile Thr Arg Lys
                165                 170                 175

Ser Thr Arg Gln Thr Thr Ile Thr Ser His Phe Ala Lys Gly Pro Ala
            180                 185                 190

Lys Arg Lys Pro Gln Glu Glu Ser Glu Arg Ala Lys Ser Asp Glu Ser
            195                 200                 205

Ile Lys Glu Glu Asp Lys Asp Gln Asp Glu Lys Arg Arg Arg Val Thr
            210                 215                 220

Ser Arg Glu Arg Val Ala Arg Pro Leu Pro Ala Glu Glu Pro Glu Arg
225                 230                 235                 240

Ala Lys Ser Gly Thr Arg Thr Glu Lys Glu Glu Glu Arg Asp Glu Lys
                245                 250                 255

Glu Glu Lys Arg Leu Arg Ser Gln Thr Lys Glu Pro Thr Pro Lys Gln
            260                 265                 270

Lys Leu Lys Glu Glu Pro Asp Arg Glu Ala Arg Ala Gly Val Gln Ala
            275                 280                 285

Asp Glu Asp Glu Asp Gly Asp Glu Lys Asp Glu Lys Lys His Arg Ser
290                 295                 300

Gln Pro Lys Asp Leu Ala Ala Lys Arg Arg Pro Glu Glu Lys Glu Pro
305                 310                 315                 320

Glu Lys Val Asn Pro Gln Ile Ser Asp Glu Lys Asp Glu Asp Glu Lys
                325                 330                 335

Glu Glu Lys Arg Arg Lys Thr Thr Pro Lys Glu Pro Thr Glu Lys Lys
            340                 345                 350

Met Ala Arg Ala Lys Thr Val Met Asn Ser Lys Thr His Pro Pro Lys
            355                 360                 365

Cys Ile Gln Cys Gly Gln Tyr Leu Asp Asp Pro Asp Leu Lys Tyr Gly
            370                 375                 380

Gln His Pro Pro Asp Ala Val Asp Glu Pro Gln Met Leu Thr Asn Glu
385                 390                 395                 400

Lys Leu Ser Ile Phe Asp Ala Asn Glu Ser Gly Phe Glu Ser Tyr Glu
```

-continued

```
                405                 410                 415
Ala Leu Pro Gln His Lys Leu Thr Cys Phe Ser Val Tyr Cys Lys His
            420                 425                 430

Gly His Leu Cys Pro Ile Asp Thr Gly Leu Ile Glu Lys Asn Ile Glu
        435                 440                 445

Leu Phe Phe Ser Gly Ser Ala Lys Pro Ile Tyr Asp Asp Pro Ser
450                 455                 460

Leu Glu Gly Gly Val Asn Gly Lys Asn Leu Gly Pro Ile Asn Glu Trp
465                 470                 475                 480

Trp Ile Thr Gly Phe Asp Gly Glu Lys Ala Leu Ile Gly Phe Ser
                485                 490                 495

Thr Ser Phe Ala Glu Tyr Ile Leu Met Asp Pro Ser Pro Glu Tyr Ala
            500                 505                 510

Pro Ile Phe Gly Leu Met Gln Glu Lys Ile Tyr Ile Ser Lys Ile Val
        515                 520                 525

Val Glu Phe Leu Gln Ser Asn Ser Asp Ser Thr Tyr Glu Asp Leu Ile
    530                 535                 540

Asn Lys Ile Glu Thr Thr Val Pro Pro Ser Gly Leu Asn Leu Asn Arg
545                 550                 555                 560

Phe Thr Glu Asp Ser Leu Leu Arg His Ala Gln Phe Val Val Glu Gln
                565                 570                 575

Val Glu Ser Tyr Asp Glu Ala Gly Asp Ser Asp Glu Gln Pro Ile Phe
            580                 585                 590

Leu Thr Pro Cys Met Arg Asp Leu Ile Lys Leu Ala Gly Val Thr Leu
        595                 600                 605

Gly Gln Arg Arg Ala Gln Ala Arg Gln Thr Ile Arg His Ser Thr
    610                 615                 620

Arg Glu Lys Asp Arg Gly Pro Thr Lys Ala Thr Thr Lys Leu Val
625                 630                 635                 640

Tyr Gln Ile Phe Asp Thr Phe Phe Ala Glu Gln Ile Glu Lys Asp Asp
                645                 650                 655

Arg Glu Asp Lys Glu Asn Ala Phe Lys Arg Arg Cys Gly Val Cys
            660                 665                 670

Glu Val Cys Gln Gln Pro Glu Cys Gly Lys Cys Lys Ala Cys Lys Asp
        675                 680                 685

Met Val Lys Phe Gly Gly Ser Gly Arg Ser Lys Gln Ala Cys Gln Glu
    690                 695                 700

Arg Arg Cys Pro Asn Met Ala Met Lys Glu Ala Asp Asp Glu Glu
705                 710                 715                 720

Val Asp Asp Asn Ile Pro Glu Met Pro Ser Pro Lys Lys Met His Gln
                725                 730                 735

Gly Lys Lys Lys Lys Gln Asn Lys Asn Arg Ile Ser Trp Val Gly Glu
            740                 745                 750

Ala Val Lys Thr Asp Gly Lys Lys Ser Tyr Tyr Lys Lys Val Cys Ile
        755                 760                 765

Asp Ala Glu Thr Leu Glu Val Gly Asp Cys Val Ser Val Ile Pro Asp
    770                 775                 780

Asp Ser Ser Lys Pro Leu Tyr Leu Ala Arg Val Thr Ala Leu Trp Glu
785                 790                 795                 800

Asp Ser Ser Asn Gly Gln Met Phe His Ala His Trp Phe Cys Ala Gly
                805                 810                 815

Thr Asp Thr Val Leu Gly Ala Thr Ser Asp Pro Leu Glu Leu Phe Leu
            820                 825                 830
```

-continued

```
Val Asp Glu Cys Glu Asp Met Gln Leu Ser Tyr Ile His Ser Lys Val
        835                 840                 845

Lys Val Ile Tyr Lys Ala Pro Ser Glu Asn Trp Ala Met Glu Gly Gly
    850                 855                 860

Met Asp Pro Glu Ser Leu Leu Glu Gly Asp Gly Lys Thr Tyr Phe
865                 870                 875                 880

Tyr Gln Leu Trp Tyr Asp Gln Asp Tyr Ala Arg Phe Glu Ser Pro
                885                 890                 895

Lys Thr Gln Pro Thr Glu Asp Asn Lys Phe Lys Phe Cys Val Ser Cys
            900                 905                 910

Ala Arg Leu Ala Glu Met Arg Gln Lys Glu Ile Pro Arg Val Leu Glu
        915                 920                 925

Gln Leu Glu Asp Leu Asp Ser Arg Val Leu Tyr Tyr Ser Ala Thr Lys
    930                 935                 940

Asn Gly Ile Leu Tyr Arg Val Gly Asp Gly Val Tyr Leu Pro Pro Glu
945                 950                 955                 960

Ala Phe Thr Phe Asn Ile Lys Leu Ser Ser Pro Val Lys Arg Pro Arg
                965                 970                 975

Lys Glu Pro Val Asp Glu Asp Leu Tyr Pro Glu His Tyr Arg Lys Tyr
            980                 985                 990

Ser Asp Tyr Ile Lys Gly Ser Asn Leu Asp Ala Pro Glu Pro Tyr Arg
        995                 1000                1005

Ile Gly Arg Ile Lys Glu Ile Phe Cys Pro Lys Lys Ser Asn Gly
    1010                1015                1020

Arg Pro Asn Glu Thr Asp Ile Lys Ile Arg Val Asn Lys Phe Tyr
    1025                1030                1035

Arg Pro Glu Asn Thr His Lys Ser Thr Pro Ala Ser Tyr His Ala
    1040                1045                1050

Asp Ile Asn Leu Leu Tyr Trp Ser Asp Glu Glu Ala Val Val Asp
    1055                1060                1065

Phe Lys Ala Val Gln Gly Arg Cys Thr Val Glu Tyr Gly Glu Asp
    1070                1075                1080

Leu Pro Glu Cys Val Gln Val Tyr Ser Met Gly Gly Pro Asn Arg
    1085                1090                1095

Phe Tyr Phe Leu Glu Ala Tyr Asn Ala Lys Ser Lys Ser Phe Glu
    1100                1105                1110

Asp Pro Pro Asn His Ala Arg Ser Pro Gly Asn Lys Gly Lys Gly
    1115                1120                1125

Lys Gly Lys Gly Lys Gly Lys Pro Lys Ser Gln Ala Cys Glu Pro
    1130                1135                1140

Ser Glu Pro Glu Ile Glu Ile Lys Leu Pro Lys Leu Arg Thr Leu
    1145                1150                1155

Asp Val Phe Ser Gly Cys Gly Gly Leu Ser Glu Gly Phe His Gln
    1160                1165                1170

Ala Gly Ile Ser Asp Thr Leu Trp Ala Ile Glu Met Trp Asp Pro
    1175                1180                1185

Ala Ala Gln Ala Phe Arg Leu Asn Asn Pro Gly Ser Thr Val Phe
    1190                1195                1200

Thr Glu Asp Cys Asn Ile Leu Leu Lys Leu Val Met Ala Gly Glu
    1205                1210                1215

Thr Thr Asn Ser Arg Gly Gln Arg Leu Pro Gln Lys Gly Asp Val
    1220                1225                1230
```

```
Glu Met Leu Cys Gly Gly Pro Pro Cys Gln Gly Phe Ser Gly Met
1235                1240                1245

Asn Arg Phe Asn Ser Arg Thr Tyr Ser Lys Phe Lys Asn Ser Leu
1250                1255                1260

Val Val Ser Phe Leu Ser Tyr Cys Asp Tyr Tyr Arg Pro Arg Phe
1265                1270                1275

Phe Leu Leu Glu Asn Val Arg Asn Phe Val Ser Phe Lys Arg Ser
1280                1285                1290

Met Val Leu Lys Leu Thr Leu Arg Cys Leu Val Arg Met Gly Tyr
1295                1300                1305

Gln Cys Thr Phe Gly Val Leu Gln Ala Gly Gln Tyr Gly Val Ala
1310                1315                1320

Gln Thr Arg Arg Arg Ala Ile Ile Leu Ala Ala Ala Pro Gly Glu
1325                1330                1335

Lys Leu Pro Leu Phe Pro Glu Pro Leu His Val Phe Ala Pro Arg
1340                1345                1350

Ala Cys Gln Leu Ser Val Val Val Asp Asp Lys Lys Phe Val Ser
1355                1360                1365

Asn Ile Thr Arg Leu Ser Ser Gly Pro Phe Arg Thr Ile Thr Val
1370                1375                1380

Arg Asp Thr Met Ser Asp Leu Pro Glu Val Arg Asn Gly Ala Ser
1385                1390                1395

Ala Leu Glu Ile Ser Tyr Asn Gly Glu Pro Gln Ser Trp Phe Gln
1400                1405                1410

Arg Gln Leu Arg Gly Ala Gln Tyr Gln Pro Ile Leu Arg Asp His
1415                1420                1425

Ile Cys Lys Asp Met Ser Ala Leu Val Ala Ala Arg Met Arg His
1430                1435                1440

Ile Pro Leu Ala Pro Gly Ser Asp Trp Arg Asp Leu Pro Asn Ile
1445                1450                1455

Glu Val Arg Leu Ser Asp Gly Thr Met Ala Arg Lys Leu Arg Tyr
1460                1465                1470

Thr His His Asp Arg Lys Asn Gly Arg Ser Ser Ser Gly Ala Leu
1475                1480                1485

Arg Gly Val Cys Ser Cys Val Glu Ala Gly Lys Ala Cys Asp Pro
1490                1495                1500

Ala Ala Arg Gln Phe Asn Thr Leu Ile Pro Trp Cys Leu Pro His
1505                1510                1515

Thr Gly Asn Arg His Asn His Trp Ala Gly Leu Tyr Gly Arg Leu
1520                1525                1530

Glu Trp Asp Gly Phe Phe Ser Thr Thr Val Thr Asn Pro Glu Pro
1535                1540                1545

Met Gly Lys Gln Gly Arg Val Leu His Pro Glu Gln His Arg Val
1550                1555                1560

Val Ser Val Arg Glu Cys Ala Arg Ser Gln Gly Phe Pro Asp Thr
1565                1570                1575

Tyr Arg Leu Phe Gly Asn Ile Leu Asp Lys His Arg Gln Val Gly
1580                1585                1590

Asn Ala Val Pro Pro Pro Leu Ala Lys Ala Ile Gly Leu Glu Ile
1595                1600                1605

Lys Leu Cys Met Leu Ala Lys Ala Arg Glu Ser Ala Ser Ala Lys
1610                1615                1620

Ile Lys Glu Glu Glu Ala Ala Lys Asp
```

<210> SEQ ID NO 3
<211> LENGTH: 386
<212> TYPE: PRT
<213> ORGANISM: Spiroplasma MQ-1

<400> SEQUENCE: 3

```
Met Ser Lys Val Glu Asn Lys Thr Lys Lys Leu Arg Val Phe Glu Ala
1               5                   10                  15

Phe Ala Gly Ile Gly Ala Gln Arg Lys Ala Leu Glu Lys Val Arg Lys
                20                  25                  30

Asp Glu Tyr Glu Ile Val Gly Leu Ala Glu Trp Tyr Val Pro Ala Ile
            35                  40                  45

Val Met Tyr Gln Ala Ile His Asn Asn Phe His Thr Lys Leu Glu Tyr
50                  55                  60

Lys Ser Val Ser Arg Glu Glu Met Ile Asp Tyr Leu Glu Asn Lys Thr
65                  70                  75                  80

Leu Ser Trp Asn Ser Lys Asn Pro Val Ser Asn Gly Tyr Trp Lys Arg
                85                  90                  95

Lys Lys Asp Asp Glu Leu Lys Ile Ile Tyr Asn Ala Ile Lys Leu Ser
            100                 105                 110

Glu Lys Glu Gly Asn Ile Phe Asp Ile Arg Asp Leu Tyr Lys Arg Thr
        115                 120                 125

Leu Lys Asn Ile Asp Leu Leu Thr Tyr Ser Phe Pro Cys Gln Asp Leu
130                 135                 140

Ser Gln Gln Gly Ile Gln Lys Gly Met Lys Arg Gly Ser Gly Thr Arg
145                 150                 155                 160

Ser Gly Leu Leu Trp Glu Ile Glu Arg Ala Leu Asp Ser Thr Glu Lys
                165                 170                 175

Asn Asp Leu Pro Lys Tyr Leu Leu Met Glu Asn Val Gly Ala Leu Leu
            180                 185                 190

His Lys Lys Asn Glu Glu Glu Leu Asn Gln Trp Lys Gln Lys Leu Glu
        195                 200                 205

Ser Leu Gly Tyr Gln Asn Ser Ile Glu Val Leu Asn Ala Ala Asp Phe
210                 215                 220

Gly Ser Ser Gln Ala Arg Arg Arg Val Phe Met Ile Ser Thr Leu Asn
225                 230                 235                 240

Glu Phe Val Glu Leu Pro Lys Gly Asp Lys Lys Pro Lys Ser Ile Lys
                245                 250                 255

Lys Val Leu Asn Lys Ile Val Ser Glu Lys Asp Ile Leu Asn Asn Leu
            260                 265                 270

Leu Lys Tyr Asn Leu Thr Glu Phe Lys Lys Thr Lys Ser Asn Ile Asn
        275                 280                 285

Lys Ala Ser Leu Ile Gly Tyr Ser Lys Phe Asn Ser Glu Gly Tyr Val
290                 295                 300

Tyr Asp Pro Glu Phe Thr Gly Pro Thr Leu Thr Ala Ser Gly Ala Asn
305                 310                 315                 320

Ser Arg Ile Lys Ile Lys Asp Gly Ser Asn Ile Arg Lys Met Asn Ser
                325                 330                 335

Asp Glu Thr Phe Leu Tyr Ile Gly Phe Asp Ser Gln Asp Gly Lys Arg
            340                 345                 350

Val Asn Glu Ile Glu Phe Leu Thr Glu Asn Gln Lys Ile Phe Val Cys
        355                 360                 365
```

```
Gly Asn Ser Ile Ser Val Glu Val Leu Glu Ala Ile Ile Asp Lys Ile
        370                 375                 380

Gly Gly
385

<210> SEQ ID NO 4
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: The residue at this position is
      5-methylcytosine
<220> FEATURE:
<221> NAME/KEY: misc_feature
<222> LOCATION: (10)..(10)
<223> OTHER INFORMATION: The residue at this position is
      5-hydroxymethylcytosine

<400> SEQUENCE: 4
tcgatcgatc gt                                                         12

<210> SEQ ID NO 5
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: The residue at this position is
      5-hydroxymethylcytosine
<220> FEATURE:
<221> NAME/KEY: misc_feature
<222> LOCATION: (6)..(6)
<223> OTHER INFORMATION: The residue at this position is
      5-methylcytosine

<400> SEQUENCE: 5
acgatcgatc ga                                                         12

<210> SEQ ID NO 6
<211> LENGTH: 12
<212> TYPE: DNA
<213> ORGANISM: Artificial Sequence
<220> FEATURE:
<223> OTHER INFORMATION: Synthetic

<400> SEQUENCE: 6
acgatcgatc ga                                                         12

<210> SEQ ID NO 7
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: The residue at this position is
      5-methylcytosine

<400> SEQUENCE: 7
acgatcgatc ga                                                         12
```

```
<210> SEQ ID NO 8
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: The residue at this position is
      5-methylcytosine
<220> FEATURE:
<221> NAME/KEY: misc_feature
<222> LOCATION: (10)..(10)
<223> OTHER INFORMATION: The residue at this position is
      5-hydroxymethylcytosine

<400> SEQUENCE: 8
tugatcgatc gt                                                            12

<210> SEQ ID NO 9
<211> LENGTH: 12
<212> TYPE: DNA
<213> ORGANISM: Artificial Sequence
<220> FEATURE:
<223> OTHER INFORMATION: Synthetic

<400> SEQUENCE: 9
ttgatcgatc gt                                                            12

<210> SEQ ID NO 10
<211> LENGTH: 20
<212> TYPE: DNA
<213> ORGANISM: Artificial
<220> FEATURE:
<223> OTHER INFORMATION: Synthetic

<400> SEQUENCE: 10
tcgatgatgt agctagtaga                                                    20

<210> SEQ ID NO 11
<211> LENGTH: 22
<212> TYPE: DNA
<213> ORGANISM: Artificial
<220> FEATURE:
<223> OTHER INFORMATION: Synthetic

<400> SEQUENCE: 11
tcgatgatgt agctagctag ca                                                 22

<210> SEQ ID NO 12
<211> LENGTH: 21
<212> TYPE: DNA
<213> ORGANISM: Artificial
<220> FEATURE:
<223> OTHER INFORMATION: Synthetic

<400> SEQUENCE: 12
tcgatgatgt agctagtagc a                                                  21

<210> SEQ ID NO 13
<211> LENGTH: 10
<212> TYPE: DNA
<213> ORGANISM: Artificial
<220> FEATURE:
<223> OTHER INFORMATION: Synthetic

<400> SEQUENCE: 13
```

```
tcgatgatgt                                                              10

<210> SEQ ID NO 14
<211> LENGTH: 10
<212> TYPE: DNA
<213> ORGANISM: Artificial
<220> FEATURE:
<223> OTHER INFORMATION: Synthetic

<400> SEQUENCE: 14
tugatgatgt                                                              10

<210> SEQ ID NO 15
<211> LENGTH: 12
<212> TYPE: DNA
<213> ORGANISM: Artificial
<220> FEATURE:
<223> OTHER INFORMATION: Synthetic

<400> SEQUENCE: 15
ttgatcgatc gt                                                           12
```